(12) United States Patent
Demanget et al.

(10) Patent No.: US 12,239,392 B2
(45) Date of Patent: Mar. 4, 2025

(54) SURGICAL TOOL AND ROBOTIC SYSTEM COMPRISING SUCH A SURGICAL TOOL

(71) Applicant: Synthes GmbH, Oberdorf (CH)

(72) Inventors: Nicolas Demanget, Gieres (FR); Alasdair Mercer, Leeds (GB); Andrew Burton, Raynham, MA (US); Stefan Gisler, Oberdorf (CH); Kevin Zylka, Blue Ash, OH (US); Yuji Ikeda, New York, NY (US); Sourav Ghosh, Leeds (GB); Matt Miller, Blue Ash, OH (US); Anthony Leandri, Gieres (FR); Bruno Alessandri, Oberdorf (CH)

(73) Assignee: Synthes GmbH, Oberdorf (CH)

( * ) Notice: Subject to any disclaimer, the term of this patent is extended or adjusted under 35 U.S.C. 154(b) by 1046 days.

(21) Appl. No.: 17/097,586

(22) Filed: Nov. 13, 2020

(65) Prior Publication Data

US 2021/0153957 A1    May 27, 2021

(30) Foreign Application Priority Data

Nov. 22, 2019  (EP) .................................... 19210955

(51) Int. Cl.
*A61B 34/30*       (2016.01)
*A61B 17/00*       (2006.01)
(Continued)

(52) U.S. Cl.
CPC .............. *A61B 34/30* (2016.02); *A61B 17/14* (2013.01); *A61B 2017/00367* (2013.01);
(Continued)

(58) Field of Classification Search
CPC . A61B 34/30; A61B 17/14; A61B 2034/2055; A61B 2017/00367;
(Continued)

(56) References Cited

U.S. PATENT DOCUMENTS

2017/0181759 A1    6/2017  Bouduban et al.
2019/0231447 A1*   8/2019  Ebbitt ................ A61B 17/1622

FOREIGN PATENT DOCUMENTS

CN         106963446 A       7/2017
CN         110226966 A       9/2019
(Continued)

*Primary Examiner* — Kevin T Truong
*Assistant Examiner* — Diana Jones
(74) *Attorney, Agent, or Firm* — Condo Roccia Koptiw LLP

(57) ABSTRACT

Surgical tools and robotic systems adaptable for treating a left side or a right side of a patient with minimal interference with the patient and surrounding operative site are disclosed. In some embodiments, a surgical tool can include a body, an end-effector, a first connector, a second connector, and a third connector. The end-effector can extend from a distal end of the body and be movable relative to the body about a pivot axis. The first connector can rigidly secure the body to a planar mechanism. The second and third connectors can rigidly secure a distal part and a proximal part of a tracker, respectively, to the body. The first and second connectors can be symmetrical to each other with respect to a plane including a longitudinal axis of the body and the pivot axis and can be suited for attachment of either the tracker or the planar mechanism.

20 Claims, 21 Drawing Sheets

(51) Int. Cl.
　　　*A61B 17/14*　　　(2006.01)
　　　*A61B 34/20*　　　(2016.01)
　　　*A61F 2/46*　　　(2006.01)
(52) U.S. Cl.
　　　CPC .............. *A61B 2017/00424* (2013.01); *A61B 2017/00477* (2013.01); *A61B 2034/2055* (2016.02); *A61B 2034/2072* (2016.02); *A61F 2/461* (2013.01)
(58) Field of Classification Search
　　　CPC ... A61B 2017/00424; A61B 2017/0477; A61F 2/461
　　　See application file for complete search history.

(56) References Cited

FOREIGN PATENT DOCUMENTS

| DE | 202009005967 U1 | 6/2009 | |
|---|---|---|---|
| WO | WO-2018103945 A1 * | 6/2018 | ............. A61B 17/02 |
| WO | WO-2018104439 A1 * | 6/2018 | ........... A61B 17/155 |
| WO | WO-2018104523 A1 * | 6/2018 | ............. A61B 17/00 |

* cited by examiner

SURGICAL TOOL AND ROBOTIC SYSTEM COMPRISING SUCH A SURGICAL TOOL

CROSS-REFERENCE TO RELATED APPLICATIONS

This application claims priority under 35 U.S.C. § 119 to European Application No. 19210955.1, filed Nov. 22, 2019, which is incorporated herein by reference in its entirety.

TECHNICAL FIELD

The present disclosure relates to a surgical tool and to a robotic system comprising such a surgical tool.

BACKGROUND

Total knee arthroplasty typically requires cutting both the femoral epiphysis and tibial epiphysis in order to remove the damaged bone and cartilage and install a knee prosthesis.

To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has to be made on the tibia T along plane T1.

In order for the surgeon to carry out all these planes accurately and in a reduced time, robotic systems have been developed.

For example, as shown in FIG. 2, a robotic system 1 comprises a motorized actuation unit 10, a planar mechanism 11 with a first end 110 attached to a terminal segment of the actuation unit, a second end 111 rigidly attached to a saw 2'. The saw comprises a body 20', a saw blade 21' movable relative to the body, and a handle 22' configured to be held by the surgeon to perform the cut. The robotic system also comprises trackers 30', 31 respectively attached to the saw and to the patient to determine in real time a relative position of the saw and the bone to be cut, and a control unit configured to compensate small movements from the patient or the surgeon, in order to maintain alignment of the saw blade with a determined plane according to which a cut has to be carried out. To activate the saw blade, the surgeon has to press a trigger 23' located on the handle 22' of the saw. The speed of the saw blade may depend on the pressure applied to the trigger.

Depending on the angular orientation of the cut to be made, the saw may have to be tilted in a position that is not comfortable for the surgeon.

FIG. 2 illustrates the robotic system with the handle 22' of the saw oriented facing up. This position is not ergonomic and the surgeon may have difficulty in controlling the saw while performing the cut. As a result, the surgeon may also cut tissues that are not intended to be affected by the surgical intervention, such as soft tissues (e.g. collateral ligaments, knee capsule and/or popliteal artery). In particular, the surgeon may not well control the pressure applied to the trigger 23', which results in a poor control of the speed of the saw blade. Besides, when the tracker 30' is an optical tracker detectable by a camera, the surgeon has to make sure not to obstruct the field of view of the camera, which could result in the tracker not being detected and the robotic system to be stopped.

Besides, since the connectors for the tracker 30' and the planar mechanism 11 are different, it is not convenient to treat opposite sides of the patient (e.g. left and right legs) with the same saw 2'.

SUMMARY OF THE DISCLOSURE

It is thus desirable to design a surgical tool adapted for treating either a left side or a right side of a patient, providing minimal interference with the patient and surrounding operative site.

Embodiments relate to a surgical tool comprising:
 a body defining a longitudinal axis,
 an end-effector extending from a distal end of the body, the end-effector being movable relative to the body about a pivot axis,
 a first connector configured to rigidly secure the body to a planar mechanism,
 a second connector configured to rigidly secure a distal part of a tracker to the body,
 wherein the first and connectors are symmetrical to each other with respect to a plane comprising the longitudinal axis and the pivot axis and are suited for attachment of either the tracker or the planar mechanism, and
 a third connector configured to rigidly secure a proximal part of the tracker to the body.

In the present text, the term "distal" and "proximal" designate parts of the surgical tool that are respectively closer to and farther from the end effector.

The symmetry of the first and second connectors allow interchangeably connecting either the planar mechanism or the tracker to each one of said connectors, which provides a greater flexibility in using the surgical tool when treating opposite sides of the patient. The third connector is advantageously also symmetrical with respect to the plane comprising the longitudinal axis and the pivot axis.

In known surgical tools, the tracker is attached to the body by only one connector; since the surgical tool vibrates during use, the vibrations may cause the tracker to move relative to the body. As a result, the signal of the system localizing the tracker may be wrongly interpreted and the position of the surgical tool may be inaccurate, thereby detrimentally affecting the accuracy of the surgical treatment.

By attaching the tracker to the body using two connectors, the tracker is less subject to move relative to the body due to vibrations during use of the surgical tool. Thus, the position of the surgical tool may be determined with a greater accuracy, which is beneficial to the quality of the surgical treatment.

In some embodiments, the tracker may extend substantially parallel to a side of the body, the tracker and the second connector being configured so as to spare a gap sufficient to pass a user's fingers between the body and the tracker.

In some embodiments, the body may comprise a recess shaped to receive a user's palm. This allows the user to firmly hold the surgical tool.

In some embodiments, the distal part of the tracker may comprise a slider operable between an unlocking position allowing the distal part of the tracker to releasably engage the first or second connector, and a locking position wherein the distal part of the tracker is locked to the first or second connector.

In some embodiments, the tracker may be a single use tracker.

Embodiments relate to a robotic system comprising such a surgical tool.

The robotic system may comprise:
- a lockable holding arm,
- an actuation unit coupled to the holding arm,
- a planar mechanism coupled to the actuation unit,
- a surgical tool as described above, wherein the body is rigidly secured to the planar mechanism by the first connector,
- a first tracker rigidly attached to the body of the surgical tool by the second and third connectors. Another tracker may be rigidly attached to the actuation unit.

In some embodiments, the tracker may extend substantially parallel to a side of the body, the tracker and the second connector being configured so as to spare a gap sufficient to pass a user's fingers between the body and the tracker.

In some embodiments, the tracker may be an optical tracker.

In some embodiments, the tracker may be a single use tracker.

In some embodiments, the actuation unit may comprise from three to five motorized degrees of freedom.

In some embodiments, the surgical tool further comprises an electric cable coupled to the body for powering an actuator of the end-effector.

Alternatively, the body may comprise a battery for powering an actuator of the end-effector.

In some embodiments, the end-effector may be a saw blade.

Some embodiments relate to a surgical tool comprising:
- a body defining a longitudinal axis,
- an end-effector extending from a distal end of the body, the end-effector being movable relative to the body,
- a first connector configured to rigidly secure the body to a planar mechanism,
- a second connector configured to rigidly secure a tracker to the body, and
- a handle selectively pivotable relative to the body, the handle comprising a grip and a trigger configured to activate the end-effector.

Such a surgical tool is more ergonomic and allows the surgeon to control precisely actuation of an end-effector, whatever the orientation of the end-effector.

In some embodiments, the handle may be selectively pivotable about an axis orthogonal to the longitudinal axis.

In some embodiments, the body may comprise a recess shaped to receive a user's hand on a side opposite to the handle.

In some embodiments, the handle may comprise two triggers configured to activate the end-effector, a first trigger being located on a distal side of the handle and a second trigger being located on a proximal side of the handle, the first trigger being closer to the body than the second trigger.

In some embodiments, the handle may be selectively pivotable about the longitudinal axis.

In some embodiments, the handle may have a substantially U shape, the handle comprising:
- a distal arm pivotally coupled to the body about the longitudinal axis,
- a proximal arm comprising the grip and the trigger, and
- a bridge connecting the distal arm and the proximal arm such that the proximal arm is offset from a proximal end of the body.

Said bridge may be selectively pivotable about the distal arm of the handle.

In some embodiments, the first and second connectors are symmetrical with respect to a plane comprising the longitudinal axis and orthogonal to the planar mechanism, the first and second connectors thus being configured to be rigidly secured to any one of the planar mechanism and the tracker.

In some of the illustrated embodiments, the handle of the surgical tool is not represented as a pivotable handle but as a fixed handle. However, these embodiments are applicable to the surgical tool whether provided with a pivotable handle or with a fixed handle. The present disclosure is thus not limited to a combination of the illustrated embodiments with a specific type of handle.

DETAILED DESCRIPTION OF EMBODIMENTS

Surgical Tool

Figure 1:
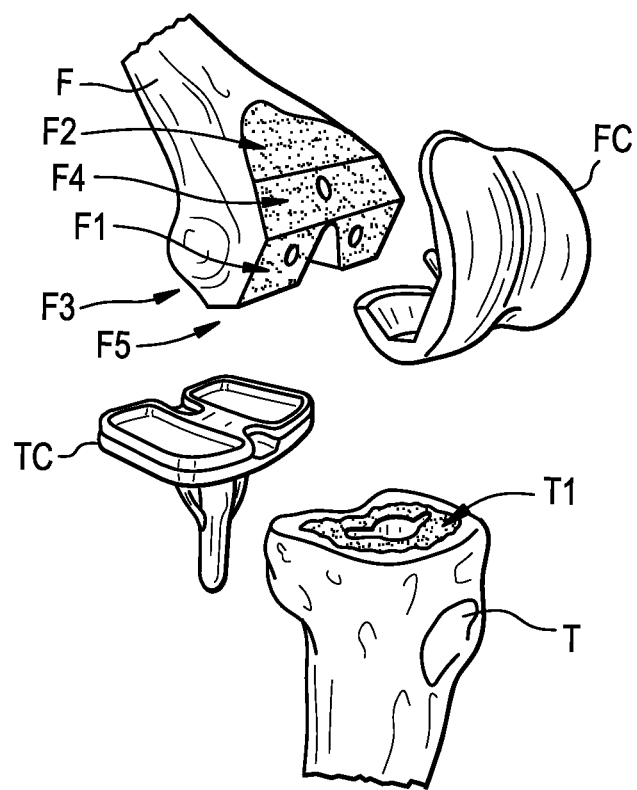
FIG. 1 schematically illustrates the cuts to be made into a femur and a tibia in total knee arthroplasty.

In the illustrated embodiments, the surgical tool is represented as a surgical saw. That is to say, the surgical tool comprises a body and an end-effector which is a saw blade. The saw blade is coupled to an actuator arranged in the body. When turned on, the actuator causes the saw blade to move relative to the body about a pivot axis. Said movement of the saw blade defines a plane called cutting plane. Said surgical tool may be used to carry out one of more planar cuts in a bone, for example in total knee arthroplasty as previously described with reference to FIG. 1.

However, non-illustrated embodiments include any other type of surgical tool comprising a body and an end-effector controlled by an actuator to be movable relative to the body. Such an end-effector may be in particular a burr or a drill bit, which rotates relative to the body. The surgical tool may be used to work a bone surface or to drill one or several bores in a bone.

The body defines a longitudinal axis extending between a proximal end and a distal end of the body. The distal end of the body is coupled to the end effector.

A handle configured for handling of the surgical tool by a user is arranged in a proximal region of the body.

The handle comprises a grip, which is a portion of the handle configured to be held in a user's hand. The handle further comprises at least one trigger, configured to activate the actuator to move the end effector when pressed by a user's finger. Preferably, the speed of movement of the end effector depends on the pressure exerted by the user on the trigger. The position of the trigger relative to the grip is chosen so that the user may press the trigger with at least one finger of the hand holding the grip.

In some embodiments the handle is selectively pivotable relative to the body. The user may thus change the orientation of the handle in order to optimize ergonomics of the surgical tool, depending on the orientation of the end effector.

The change in orientation may be continuous, i.e. any position of the handle relative to the body between two end positions is available.

Alternatively, the change in orientation may be stepwise, i.e. only a discrete number of positions of the handle relative to the body (e.g. every 5° of relative inclination) are available.

In both cases, the surgical tool may comprise a locking mechanism configured to rigidly secure the handle to the body. When the user intends to change the orientation of the handle relative to the body, he has first to unlock the locking mechanism to be allowed to move the handle. Once the desired orientation of the handle relative to the body has been achieved, the user has to lock the locking mechanism before using the surgical tool. According to an embodiment, the locking mechanism may include a button that may be pressed by the user to unlock the mechanism. The button may be urged by a spring member returning the mechanism in the locked configuration when the user releases his pressure onto the button.

Figure 2:
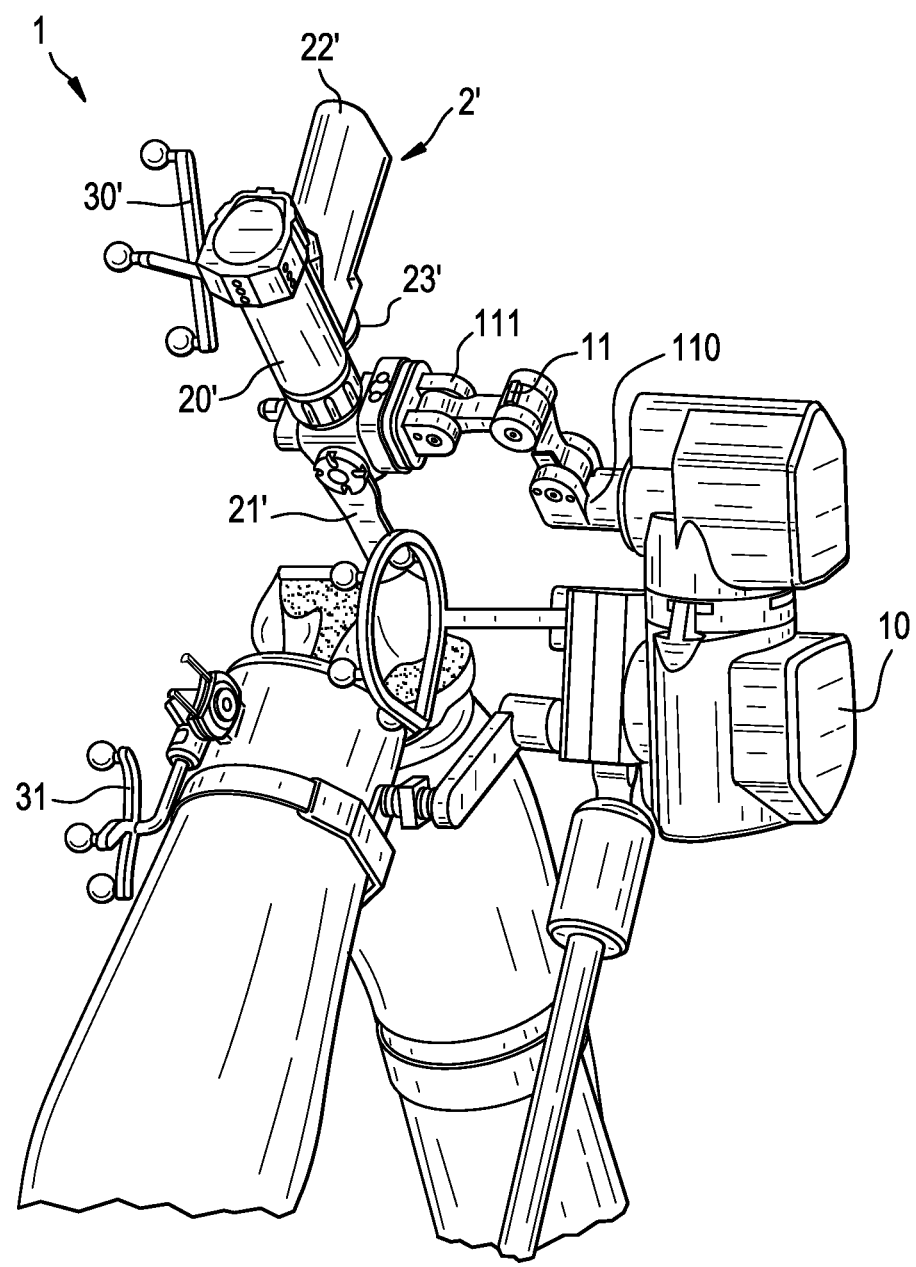
FIG. 2 illustrates an embodiment of a robotic system with a saw oriented in a non-ergonomic position.

Thanks to this selective orientation of the handle relative to the body, the situation of FIG. 2 may be avoided by placing the handle in a more ergonomic position for the user.

According to an embodiment, the handle is pivotable about an axis orthogonal to the longitudinal axis of the body.

Figure 3A:
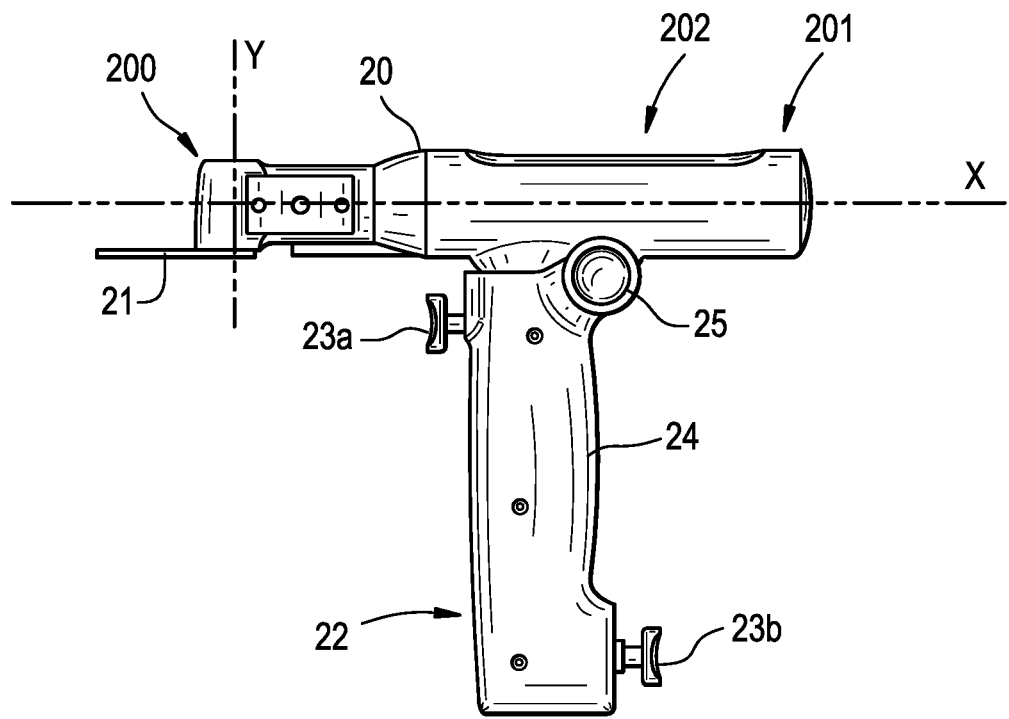
FIGS. 3A-3B illustrate an embodiment of a surgical tool wherein the handle is pivotable about an axis orthogonal to the longitudinal axis of the body.
Figure 3B:
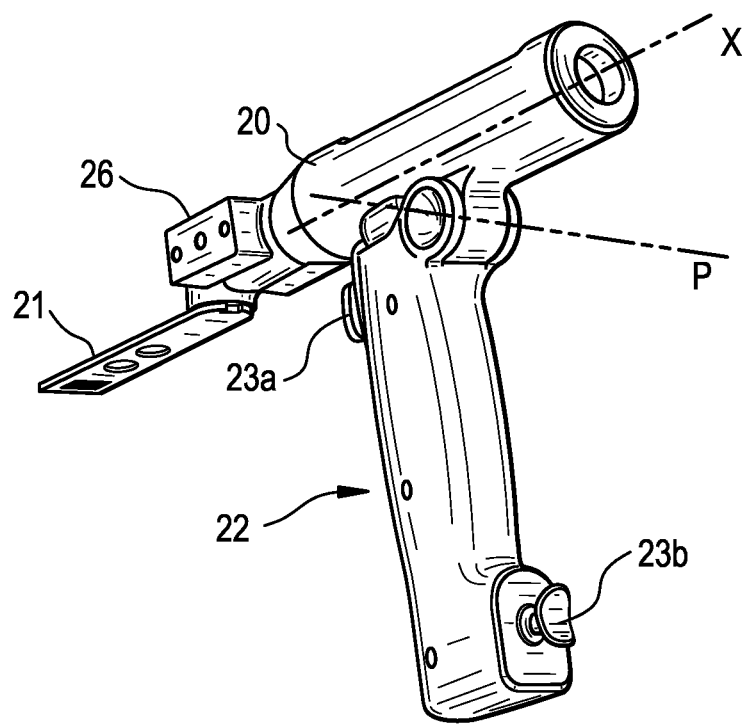

FIGS. 3A and 3B illustrate a first embodiment of the surgical tool.

The tool comprises a body 20. The body 20 presents an elongated shape along a longitudinal axis X. The body 20 comprises a distal end 200 from which extends a saw blade 21, and a proximal end 201.

Although not shown, the body includes an actuator (motor) operatively coupled to the saw blade to move the saw blade in a plane orthogonal to the sheet of FIG. 3A and parallel to the longitudinal axis, about the pivot axis Y which is orthogonal to the longitudinal axis X.

The actuator may be powered by an electric cable or by a battery embedded in the body.

In the embodiment of FIGS. 3A and 3B, the electric cable may extend from the proximal end 201 of the body, along the longitudinal axis X. In other embodiments, the electric cable may extend from any other part of the body, provided that it does not hinder proper use of the saw.

The handle 22 is pivotally mounted on the body, about an axis P which is orthogonal to the longitudinal axis X. The connection between the body and the handle comprises a locking mechanism, which may be actuated by a locking button 25.

To change the angular position of the handle relative to the body, the user may press the button 25, move the handle to the desired position which may be free or angularly indexed to a certain number of allowed positions (e.g. with an interval of 5° between adjacent positions), and release the button to lock the handle in the desired position.

The handle 22 may present a pistol shape design.

The handle comprises a generally central region that constitutes a grip 24. To that end, the shape and dimension of said central region are designed to be easily and comfortably held by a user's hand.

The handle comprises a first trigger 23a located on a distal side of the handle 22, between the body 20 and the grip 24. Thus, when the user holds the handle in his hand, one finger (e.g. the forefinger) may be placed on the trigger 23a so as to activate the actuator.

According to an advantageous embodiment, the handle may comprise a second trigger 23b, located on a proximal side of the handle, opposite the first trigger 23a relative to the grip 24. Said second trigger 23b has the same function as the first trigger 23a.

Said second trigger 23b may be particularly useful when the surgical tool is oriented in a reverse position as compared to FIG. 3A, e.g. when the handle is located above the body, as in FIG. 2. In such case, the user may hold the grip 24 in a reverse way from the one of FIG. 3, so as to place his forefinger on the second trigger 23b.

The user may thus choose to use either the first or the second trigger to hold the surgical tool in a comfortable and ergonomic way.

On its side opposite to the handle, the body 20 may comprise a recess 202 shaped to receive a user's hand. The recess provides an intuitive positioning of the hand relative to the body 20. In this way, the user may place one hand around the grip 24 and a trigger, and the other hand in the recess 202 of the body, so as to firmly hold the surgical tool.

A connector 26 extends on a side of the body, in the vicinity of the distal end. Another connector (not visible in FIGS. 3A and 3B) extends on the opposite side of the body. Each connector is configured for removable attachment of a tracker and/or a planar mechanism. The attachment may be provided by screws or pins. Preferably, attachment or removal of the tracker and/or planar mechanism is carried out without requiring any tool. For example, the attachment may be provided by lever clamps or sliders, which can be operated by a user without any tool. Embodiments of the connectors are shown in FIGS. 7A-7B and 8A-8B that will be described below.

Preferably, the connectors are symmetrical with respect to a plane containing the longitudinal axis X and perpendicular to the cutting plane. In this way, depending on the side of the patient where the surgical intervention is carried out (e.g. left leg or right leg in case of knee arthroplasty), each connector may be interchangeably attached to either the planar mechanism or the tracker to provide the most convenient configuration of the robotic device.

According to another embodiment, the handle is pivotable about the longitudinal axis.

Figure 4:
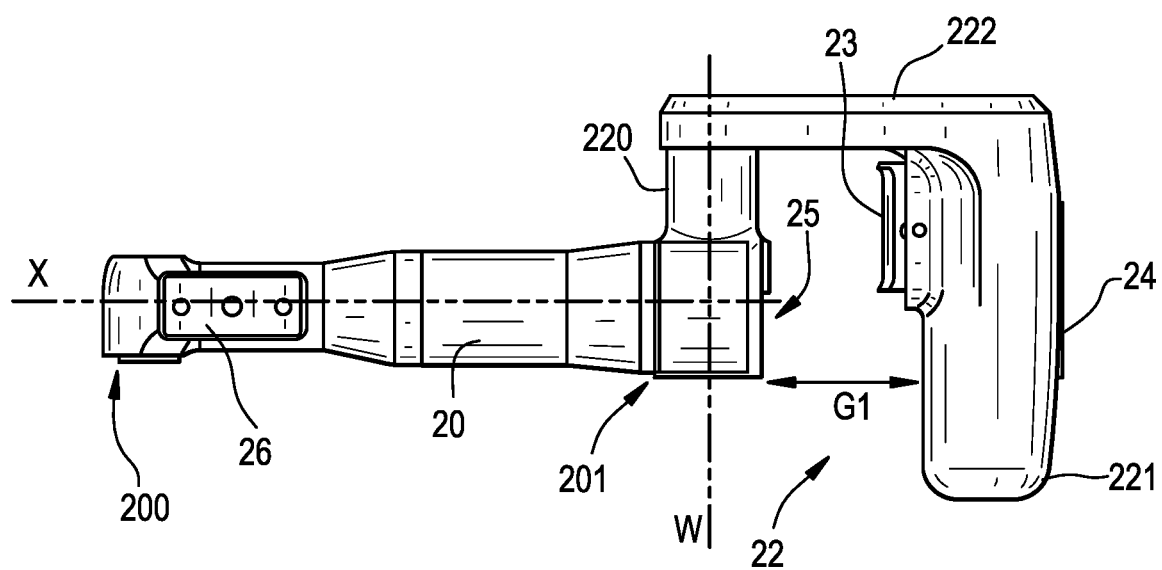
FIG. 4 illustrates an embodiment of a surgical tool wherein the handle is pivotable about the longitudinal axis of the body.

FIG. 4 illustrates a second embodiment of the surgical tool.

The tool comprises a body 20. The body 20 presents an elongated shape along a longitudinal axis X. The body 20 comprises a distal end 200 from which extends a saw blade 21, and a proximal end 201.

Although not shown, the body includes an actuator (motor) operatively coupled to the saw blade to move the saw blade in a plane orthogonal to the sheet of FIG. 4 and parallel to the longitudinal axis.

The actuator may be powered by an electric cable or by a battery embedded in the body.

In the embodiment of FIG. 4, the electric cable (not shown) may extend from the proximal end 201 of the body, in a direction orthogonal to the longitudinal axis X, e.g. opposite the connection between the body 20 and the handle 22. In other embodiments, the electric cable may extend from any other part of the body, provided that it does not hinder proper use of the saw.

The handle 22 is pivotally mounted on the body, about the longitudinal axis X. The connection between the body and the handle comprises a locking mechanism, which may be actuated by a locking button 25.

To change the angular position of the handle relative to the body, the user may press the button 25, move the handle to the desired position which may be free or angularly indexed to a certain number of allowed positions (e.g. with an interval of 5° between adjacent positions), and release the button to lock the handle in the desired position.

The handle 22 may present a substantially U shape. More precisely, the handle includes a distal arm 220 pivotally coupled to the body 20 about the longitudinal axis X, and a proximal arm 221 comprising a grip 24 and a trigger 23.

The distal and proximal arms are connected by a bridge 222 that may extend substantially parallel to the body 20, offset from the axis X.

In this way, the proximal arm 221 is offset from the proximal end 201 of the body by a gap G1. The gap G1 is designed to allow enough space for the user's fingers, thereby allowing the user to wrap his hand around the grip 24.

The trigger 23 is advantageously located on a distal side of the proximal arm, between the bridge and the grip. Thus, when the user holds the handle in his hand, one finger (e.g. the forefinger) may be placed on the trigger 23 so as to activate the actuator.

According to an embodiment, the bridge may be pivotable relative to the distal arm 220, about an axis W of the distal arm. The connection between the distal arm 220 and the bridge 222 comprises a locking mechanism, which may be actuated by a locking button (not shown).

In this way, the user may benefit from two rotational degrees of freedom to adjust the orientation of the proximal arm relative to the body and end effector of the surgical tool.

Tracker

The tracker may be any tracker usable in surgery.

Preferably, the tracker may be a single use tracker, which is intended to be disposed of after the surgical intervention. To that end, the tracker may be made in a plastic material and provided in a sterile sheet. An advantage of using such a single use tracker is to reduce sterilization costs that are incurred with reusable surgical devices. Another advantage is to provide a great precision of the position of the trackable elements with respect to the body. Indeed, reusable trackers may deform following repeated use and sterilization, thereby losing accuracy.

The tracker may be in particular an optical tracker, but other tracking technologies, e.g. electromagnetic, are not excluded.

According to an advantageous embodiment, the tracker may comprise an elongated shape substantially parallel to the body.

The tracker may be provided as a single part in order to reduce the number of parts involved in the system, in order to reduce inaccuracy due to the assembly of several parts and to save assembly time and cost. However, in some embodiments, the tracker may comprise a tracker holder, which is removably attached to the body, and trackable elements attached to the tracker holder.

Preferably, the connection between the tracker and the body is designed so as to provide a gap G2 (see FIGS. 5C and 6C) between the body and the tracker, sufficient to allow passage of the user's fingers. Thus, when the user holds the body 20 by placing the palm of his hand in the recess 202, he may wrap the body with his fingers passing between the body and the tracker.

The attachment of the tracker to the body is reversible. In particular, the tracker may be removed to be cleaned and sterilized in case of a reusable tracker, or to be disposed of in case of a single use tracker.

In addition to being attached to the distal end of the body via the above-mentioned connector, the tracker is also advantageously attached to the proximal end of the body. In this way, the fixation of the tracker to the body is stable, which ensures that the position of the tracker relative to the body remains fixed during the surgical intervention, despite vibrations or shocks to which the tracker may be exposed.

FIGS. 5A-5C and 6A-6D illustrate two alternative embodiments for the attachment of the tracker. In the illustrative drawings, the handle 22 appears to be rigidly connected to the body 20, but it may also be pivotable relative to the body as described above.

Figure 5A:
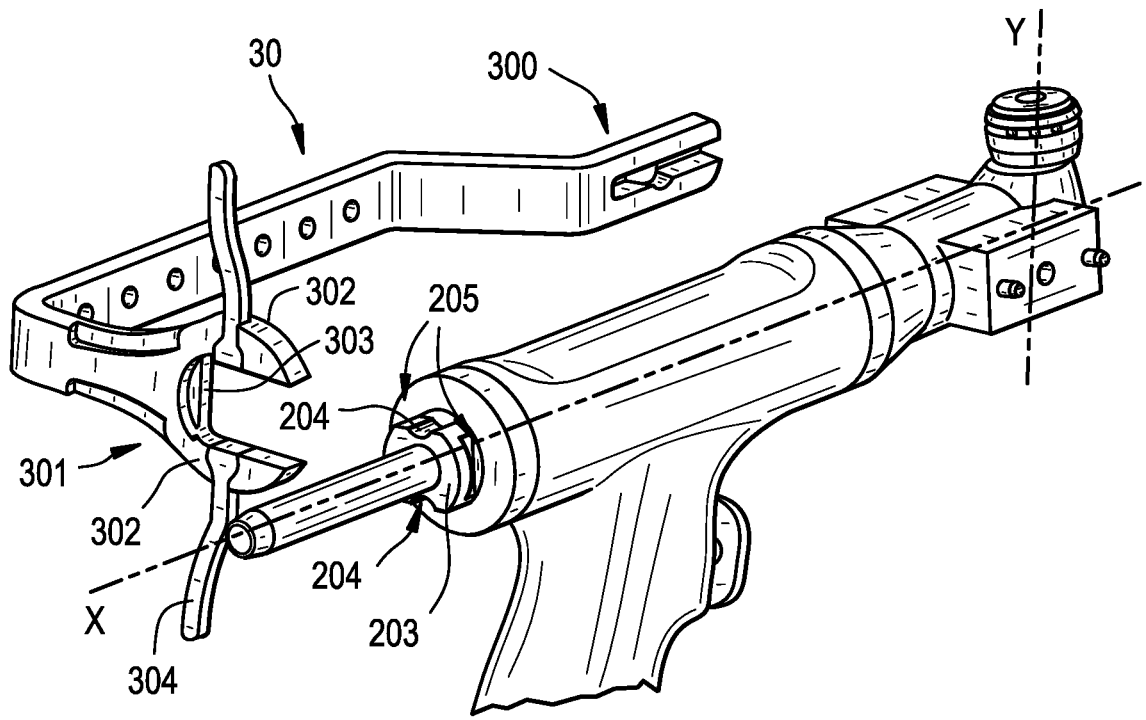
FIGS. 5A to 5C illustrate an embodiment of an attachment of a tracker to the surgical tool.
Figure 5B:
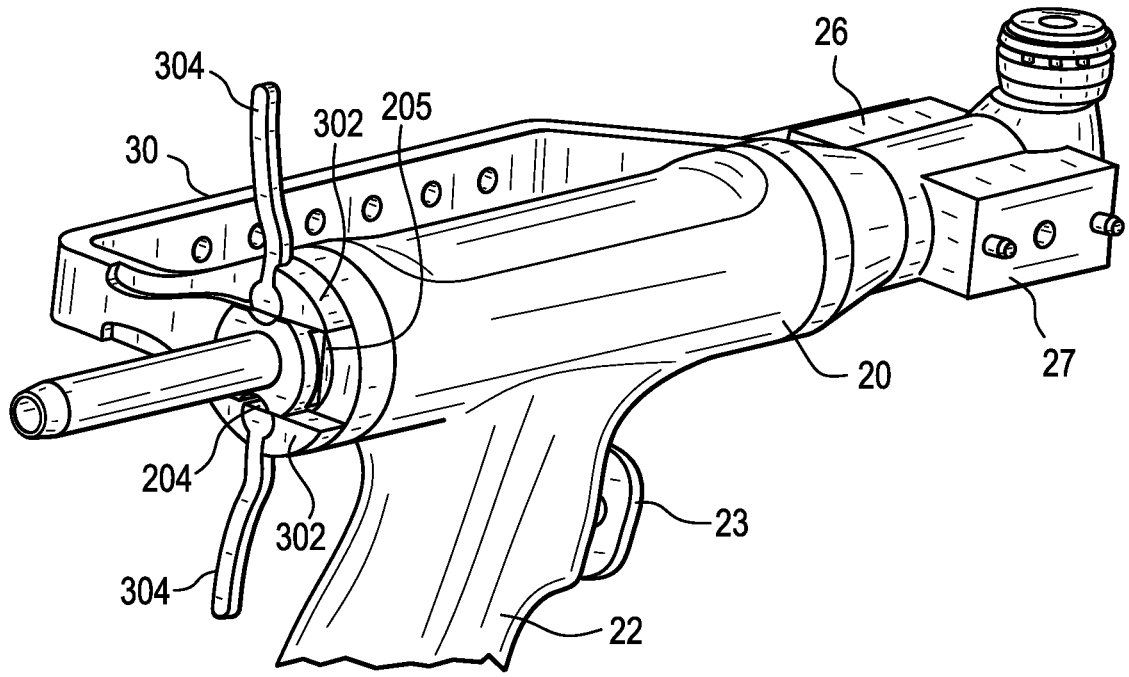
Figure 5C:
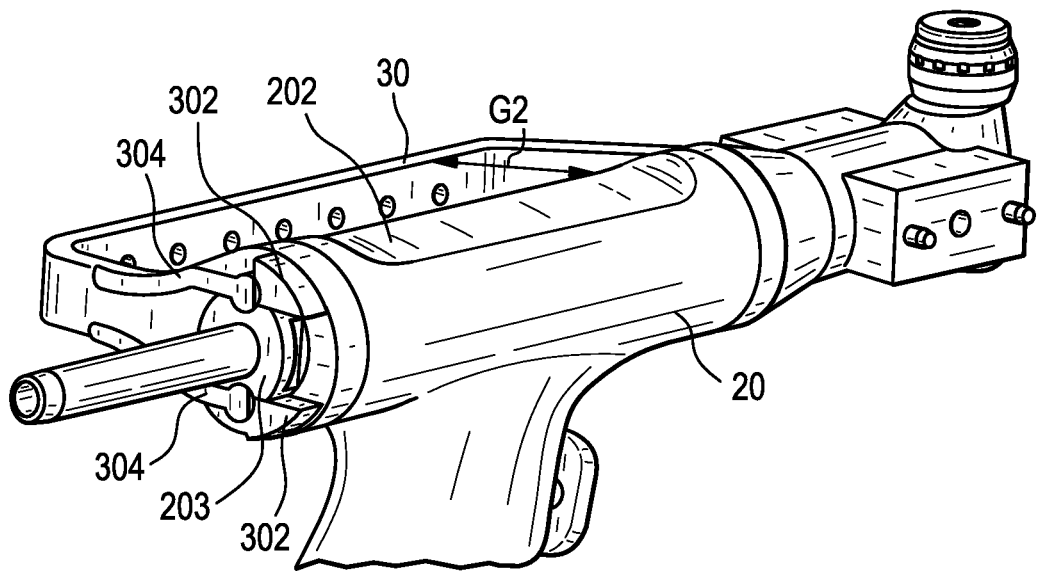

With reference to FIGS. 5A-5C, the tracker (or tracker holder) 30 presents an elongated shape with a distal end 300 configured to be coupled to the connector 26 and/or 27 of the body, and a proximal end 301 having a substantially U shape extending in a plane substantially orthogonal to the longitudinal axis X.

The proximal end 201 of the body comprises a connecting piece 203 having a substantially round shape with opposite recesses 204 on upper and lower sides, and opposite grooves 205 on right and left sides.

The proximal end 301 of the tracker comprises upper and lower arms 302 extending on either sides of the connecting piece 203. The arms are connected by an intermediate portion which comprises a tongue 303 engaging one of the grooves 205.

The proximal end 301 of the tracker further comprises upper and lower levers 304.

Before mounting the tracker onto the body, the levers are arranged in an unlocking position (see FIGS. 5A-5B) so as not to interfere with the connecting piece 203, thereby allowing the lower and upper arms to be inserted around the connecting piece.

Once the proximal end 301 of the tracker has been mounted on the connecting piece, with the tongue 303 being inserted in the respecting groove 205, the levers 304 are pivoted to a locking position where each lever engages a respective recess 204 (see FIG. 5C). In this locking position, the levers securely attach the proximal end of the tracker to the body.

When the tracker has to be detached from the body, a user simply has to pivot the levers to the unlocking position and to remove the proximal end from the connecting piece.

Since the connecting piece 203 and the connectors 26, 27 are symmetrical with respect to a plane comprising the longitudinal axis X of the body and the pivot axis Y of the saw blade, the tracker may be mounted on either side of the body and attached to either connector 26 or connector 27.

With reference to FIGS. 6A-6D, the tracker (or tracker holder) 30 presents an elongated shape with a distal end 300 configured to be coupled to the connector 26 and/or 27 of the body, and a proximal end 301 having a substantially U shape extending in a plane substantially orthogonal to the longitudinal axis X.

The proximal end 201 of the body comprises a connecting piece 203 having a substantially round shape. Besides, grooves 206 are provided on right and left sides of the body, in the region of the proximal end.

The proximal end 301 of the tracker comprises left and right arms 302 having a rounded shape fitting the connecting piece 203. Each arm comprises a flange 305 extending in the distal direction. Each flange 305 is provided with a respective inner rim 306.

Figure 6A:
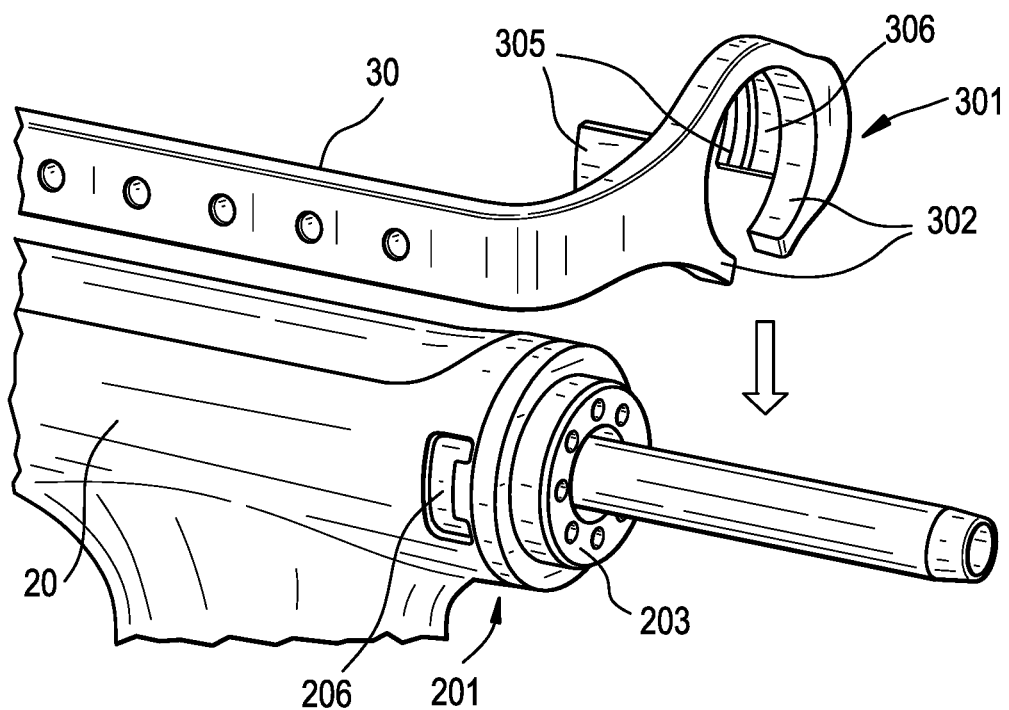
FIGS. 6A to 6D illustrate another embodiment of an attachment of a tracker to the surgical tool.
Figure 6B:
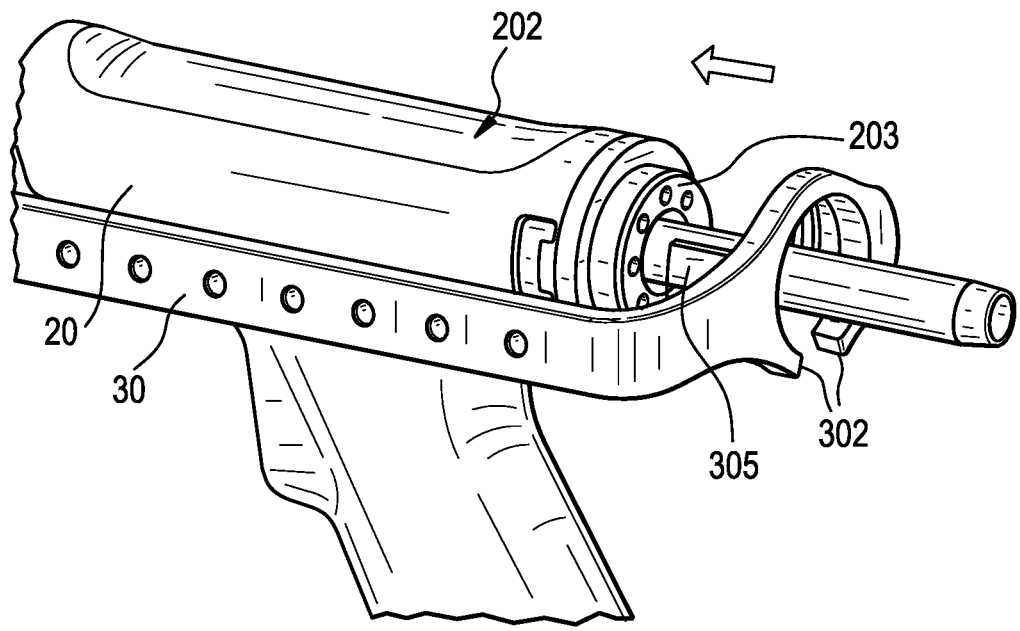
Figure 6C:
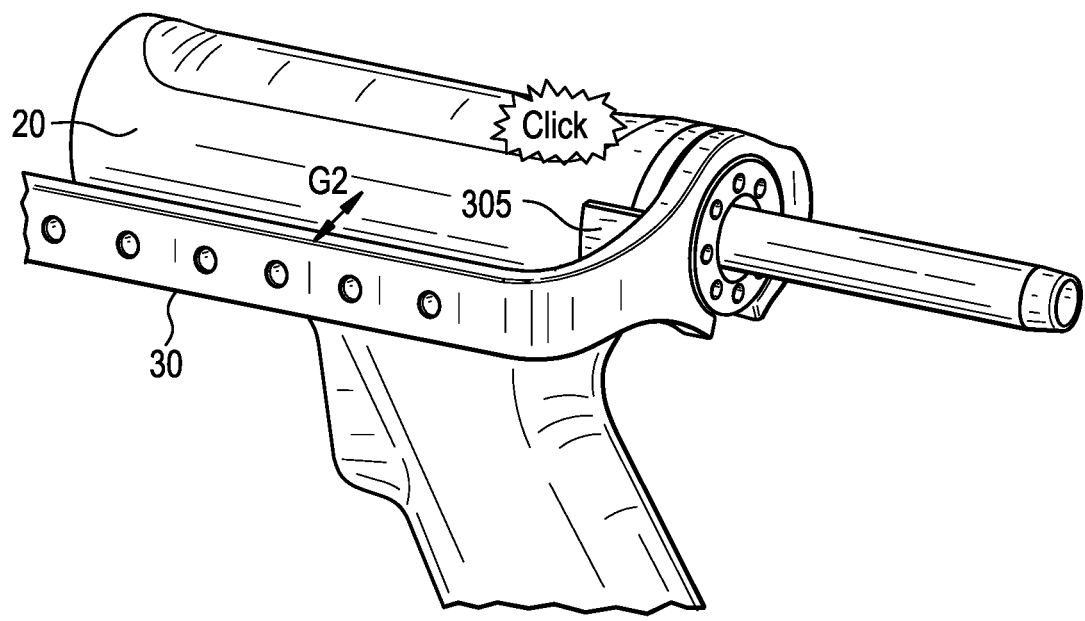
Figure 6D:
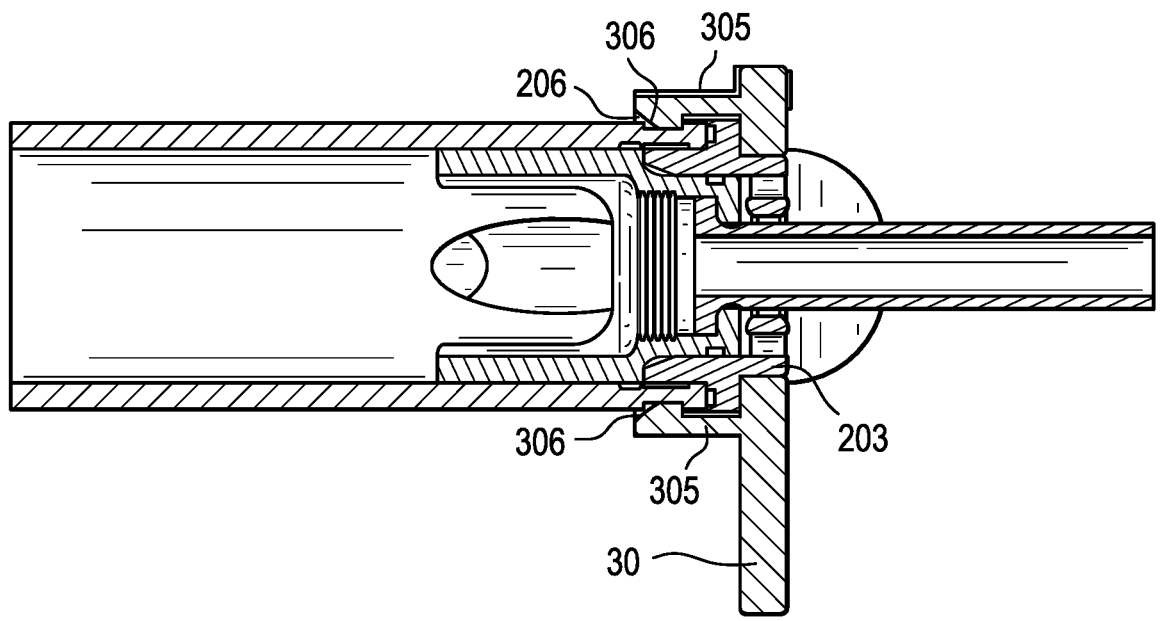

To attach the tracker to the body, the proximal end is first placed proximally from the connecting piece 203 (see FIG. 6A) and then moved along the longitudinal axis in the distal direction (see FIG. 6B) until the arms fit the connecting piece 203 (see FIG. 6C). In this last position, the rims 306 engage the grooves 206, thereby securing the proximal end of the tracker relative to the body. During engagement of the proximal end onto the connecting piece, the flanges 305 may slightly deform until the rims 306 engage the grooves 206. To that end, the tracker (or tracker holder) is preferably made of plastic.

Then, the distal end of the tracker is attached to the distal end of the body via the connector.

Since the connecting piece 203, the grooves 206 and the connectors 26, 27 are symmetrical with respect to a plane comprising the longitudinal axis X of the body and the pivot axis Y of the saw blade, the tracker may be mounted on either side of the body and attached to either connector 26 or connector 27.

Depending on the design of the connectors, various ways of attaching the tracker and the planar mechanism to the body may be provided.

Figure 7A:
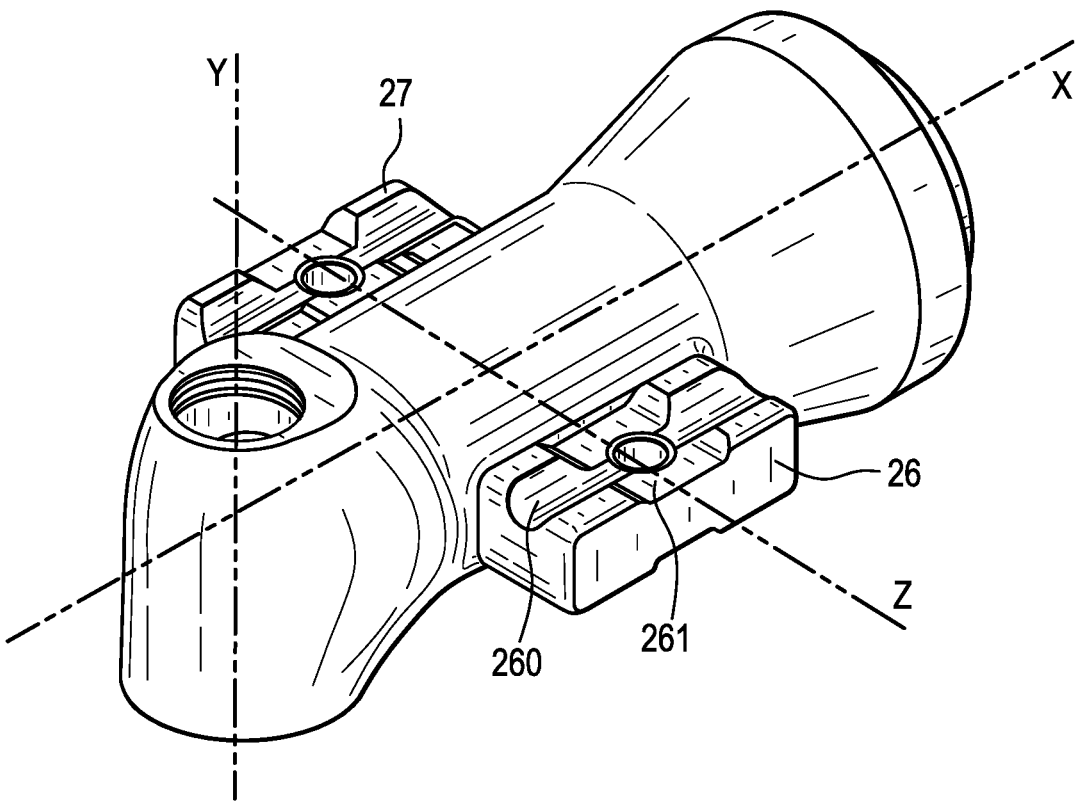
FIGS. 7A-7C illustrate an embodiment of the connection of the tracker to the body.
Figure 7B:
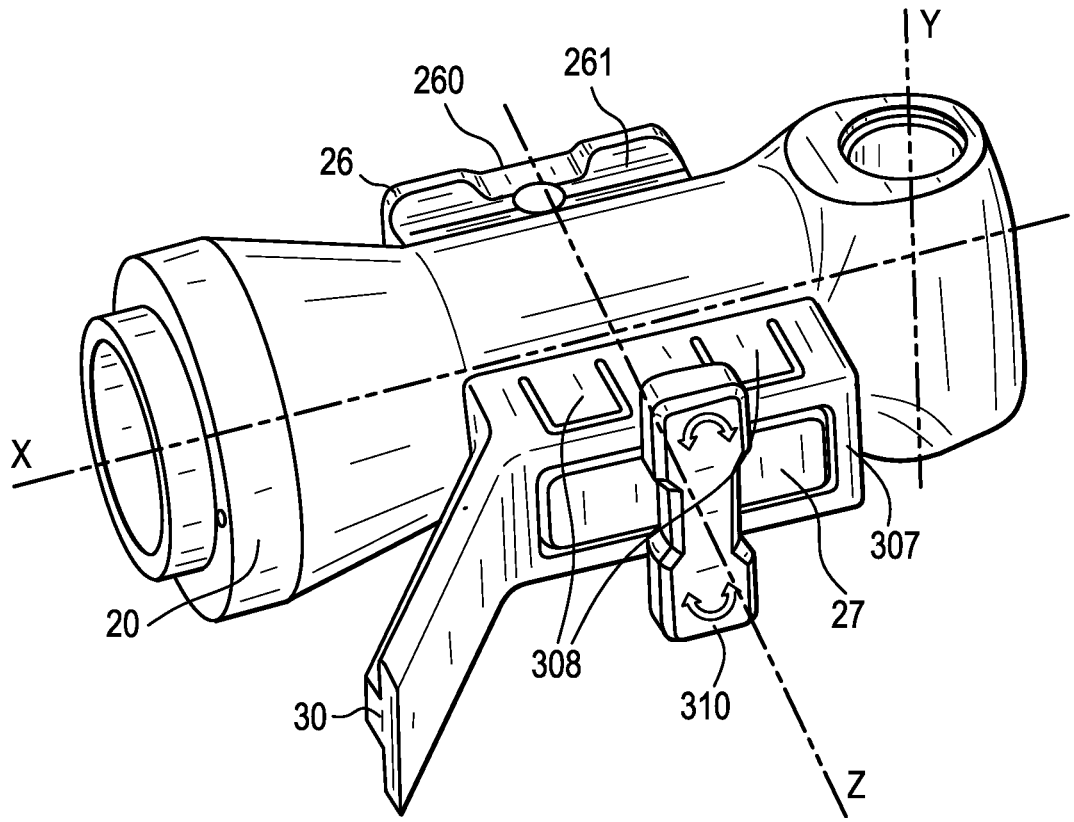
Figure 7C:
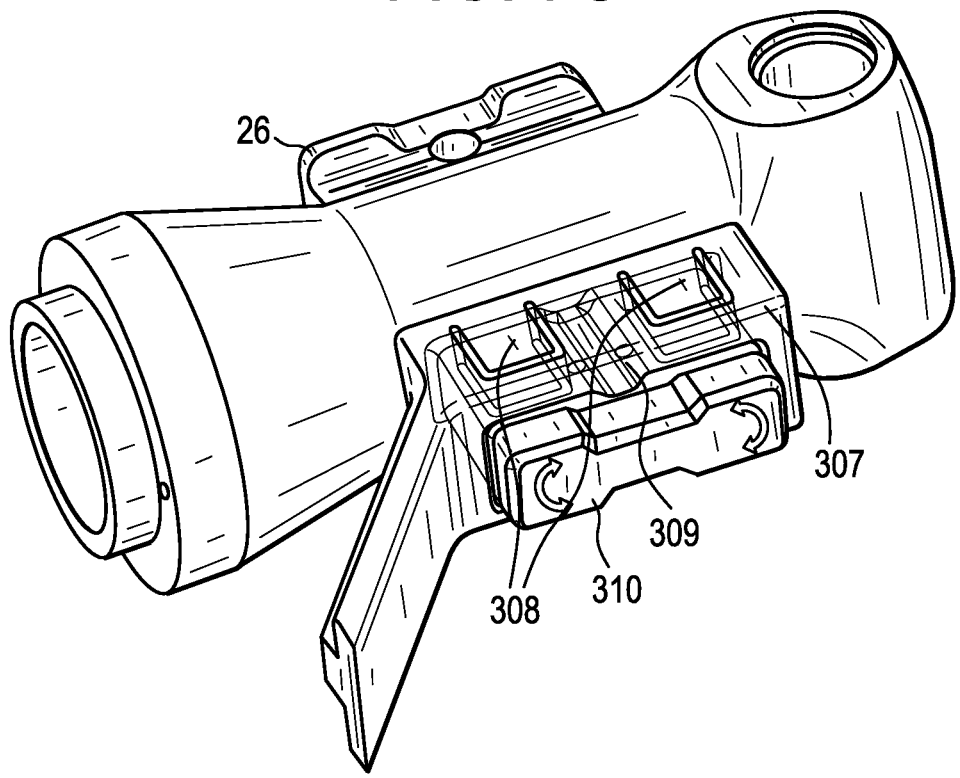

FIGS. 7A-7C illustrate an embodiment of the connection of the tracker to the distal end of the body which does not involve any tool.

Only the distal part of the body 20 is represented in these figures.

The connectors 26, 27 are symmetrical relative to a plane comprising the longitudinal axis X of the body and the pivot axis Y of the saw blade. Thus, the description of the design of one connector also applies to the other connector.

The connector 26 has a parallelepiped shape which extends from the body 20 in a direction Z orthogonal to axes X and Y. The upper side of connector 26 is provided with two intersecting grooves 260, 261. The groove 260 is parallel to the longitudinal axis X. The groove 261 is orthogonal to the groove 260.

The proximal end of the tracker 30 comprises a parallelepiped female connector 307 configured to engage the connector 26 or 27. As better seen on FIG. 7C, the upper side of the connector 307 comprises flexibles legs 308 extending in the direction of axis Z, which are configured to engage the groove 260. The upper side of the connector 307 further comprises an inner rib 309, located between the flexible legs 308, which is configured to engage the groove 261. Although the lower side of the connector 307 is not visible, similar flexible legs and inner rib are provided in this lower side.

The cooperation of the grooves 260, 261 and the flexible legs 308 and inner ribs 309 allow retaining the tracker (or the planar mechanism) in both directions X and Z.

The female connector 307 of the tracker may be further removably secured to the connector 26 or 27 by a pivotable lock 310 that is part of the respective connector.

Figure 8:
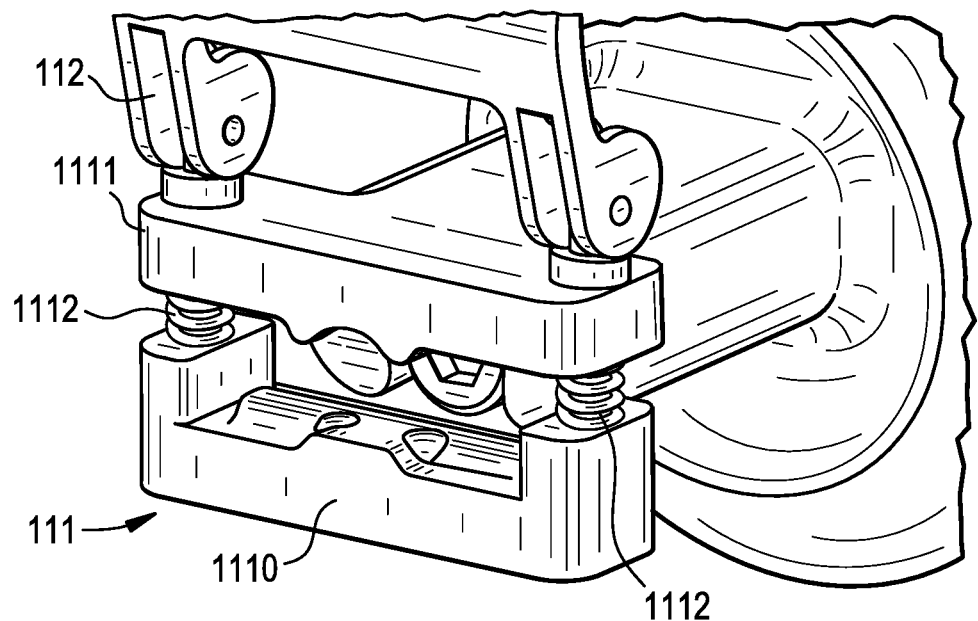
FIG. 8 illustrates an embodiment of the connection of the planar mechanism to the body.

FIG. 8 illustrates an embodiment of the connection of the planar mechanism to the body which does not involve any tool. The connectors 26, 27 of the body are the same as in FIGS. 7A-7C.

The connector provided at the end 111 of the planar mechanism comprises two clamping jaws 1110, 1111 mobile relative to each other, between an open position (shown in FIG. 8) and a closed position wherein the planar mechanism is secured to the connector 26 or 27 of the body by the jaws. The jaws are urged in the open position by springs 1112. In the illustrated embodiment, the upper jaw 1111 is fixed relative to the planar mechanism and the lower jaw 1110 is mobile relative to the upper jaw.

The internal shape of the jaws is complementary to the outer shape of the connectors 26, 27.

The connector further comprises an eccentric lever 112, configured to cause the jaws 1110, 1112 to close against the force exerted by the springs 1112 when pivoted in a closing direction. Conversely, pivoting the lever in an opening direction opposite to the closing direction causes the jaws to open with assistance of the springs.

Figure 9A:
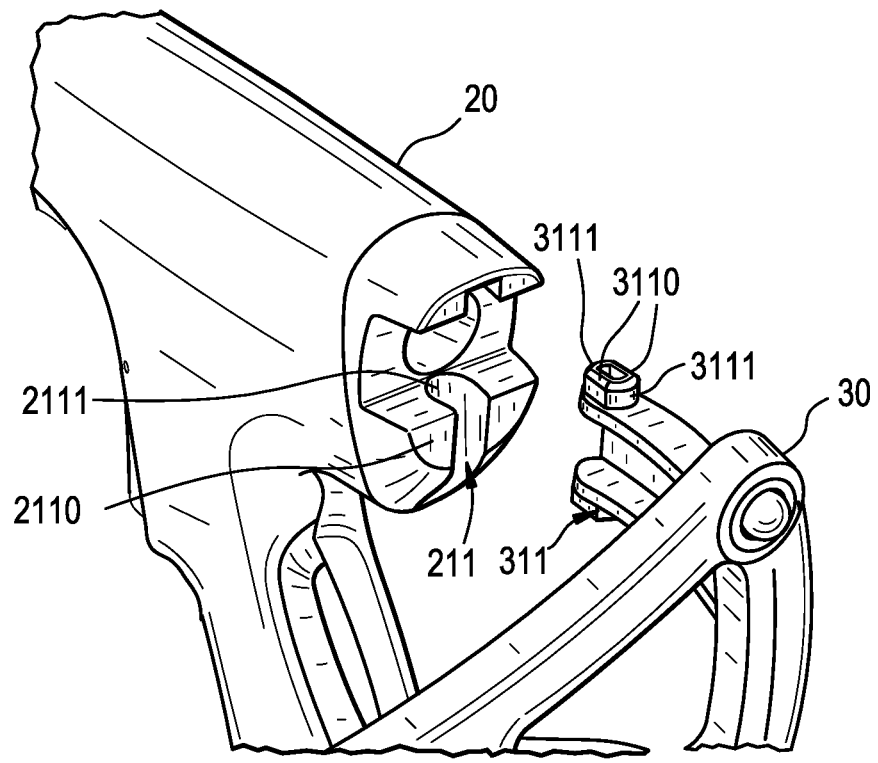
FIGS. 9A-9B illustrate an embodiment of the connection of the tracker to the proximal part of the body.
Figure 9B:
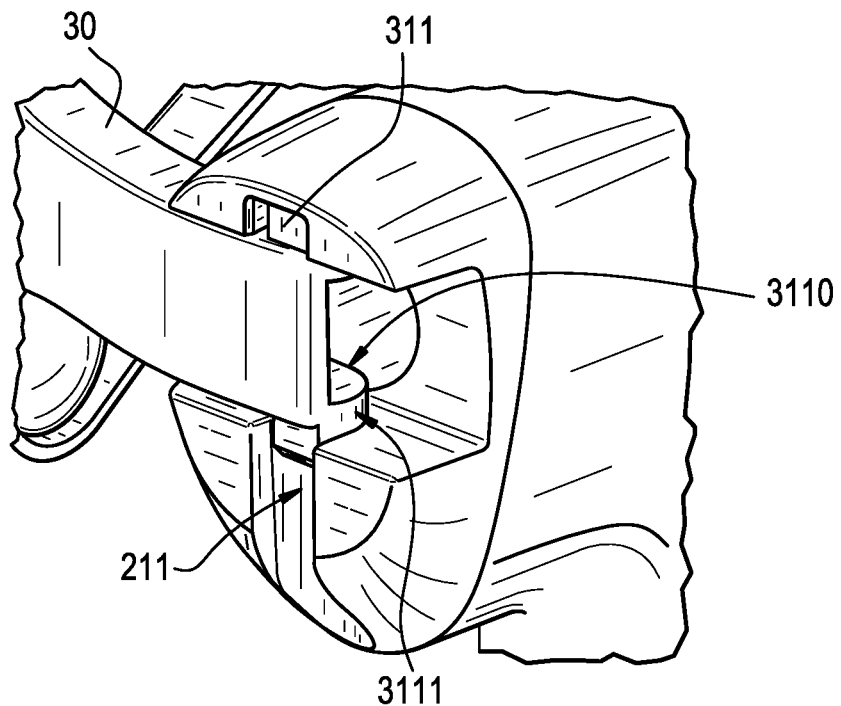

FIGS. 9A-9B illustrate a further embodiment of the connection of the tracker to the proximal part of the body. The proximal part of the tracker comprises a shaft 311 configured to be pivotally mounted into a corresponding housing 211 provided at the proximal end of the body. The shaft 311 does not have a circular cross section. Rather, the shaft comprises two opposite linear sides 3110 that are connected by opposite semicircular sides 3111. The distance between the linear sides 3110 is smaller than the distance between the semicircular sides 3111. The housing 211 comprises a slot 2110 which is narrower than the inner volume 2111 of the housing. As a result, the shaft 311 can be introduced in the housing only by passing the linear sides 3110 through the slot. Then, pivoting the shaft relative to the housing by about 90° causes the shaft to be retained in the housing.

Figure 10A:
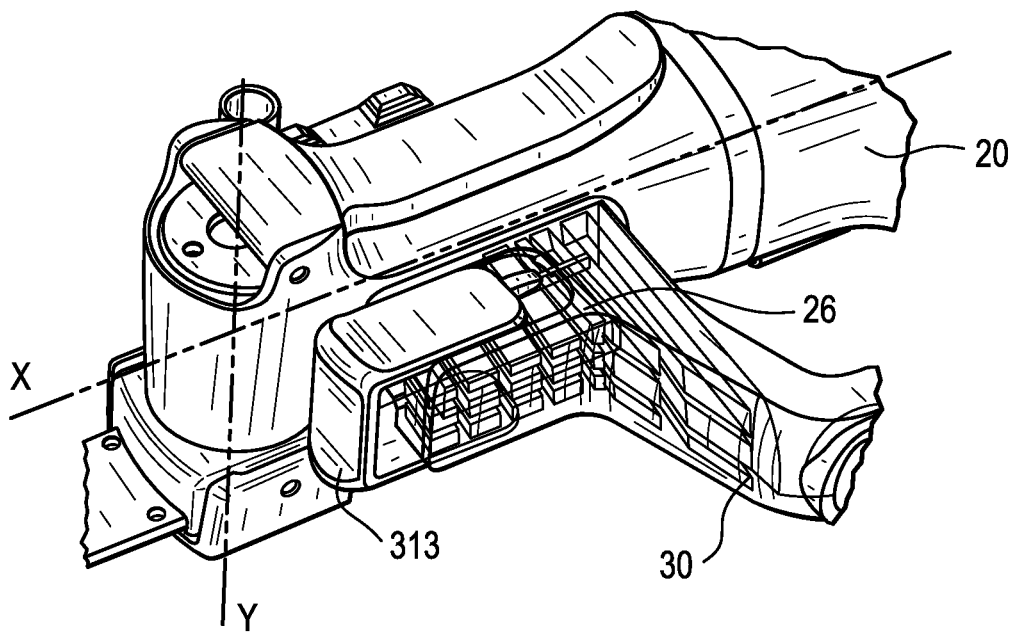
FIGS. 10A-10B illustrate an embodiment of the connection of the tracker to the distal part of the body.
Figure 10B:
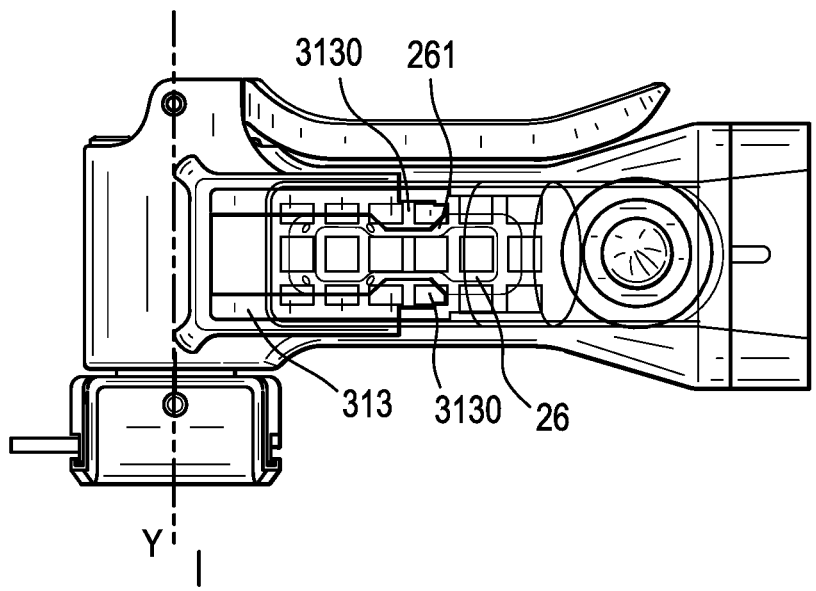

FIGS. 10A-10B illustrate an embodiment of the connection of the tracker to the distal part of the body. This tracker may in particular be the same as the one described with reference to FIGS. 9A-9B.

The distal part of the body 20 is provided with connectors 26, 27 as shown in FIG. 7A.

The distal end of the tracker 30 is provided with a slider 313 which is movable in translation between an unlocking position and a locking position.

In the locking position shown in FIG. 10B, the slider 313 comprises internal protrusions 3130 that fit the grooves 260, 261. In this way, the tracker is fixed in translation and rotation relative to the connector 26.

Figure 11A:
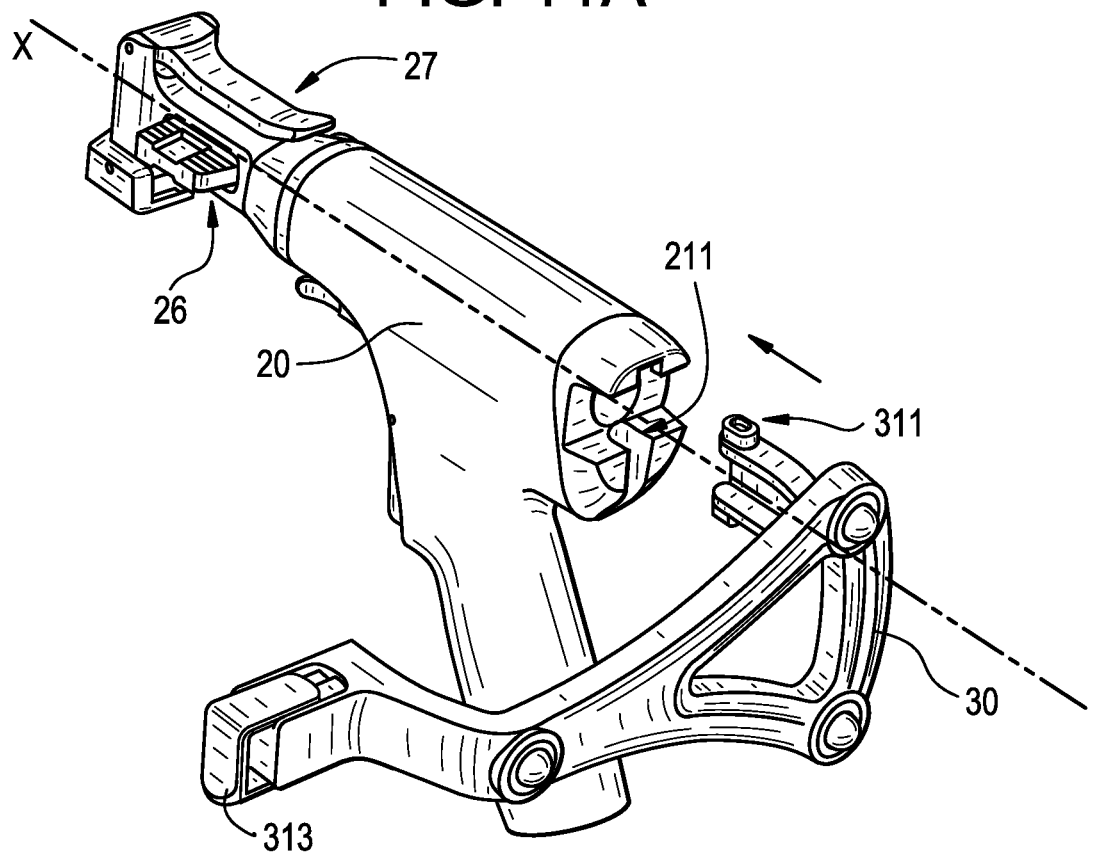
FIGS. 11A-11C illustrate steps of a method for connecting the tracker to the body using the connectors of FIGS. 9A-9B and 10A-10B.
Figure 11B:
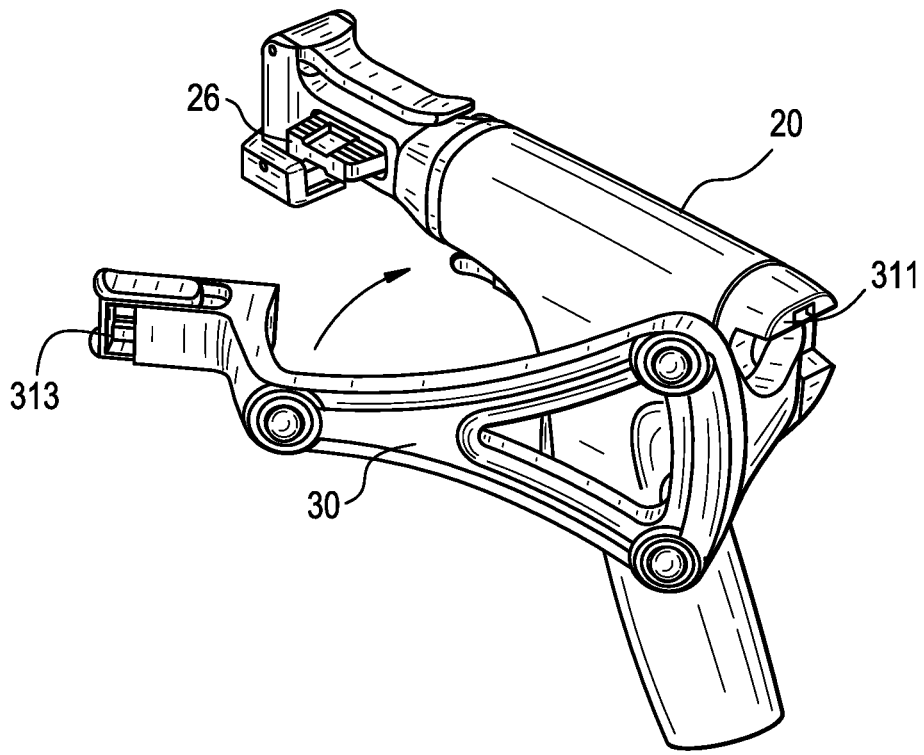
Figure 11C:
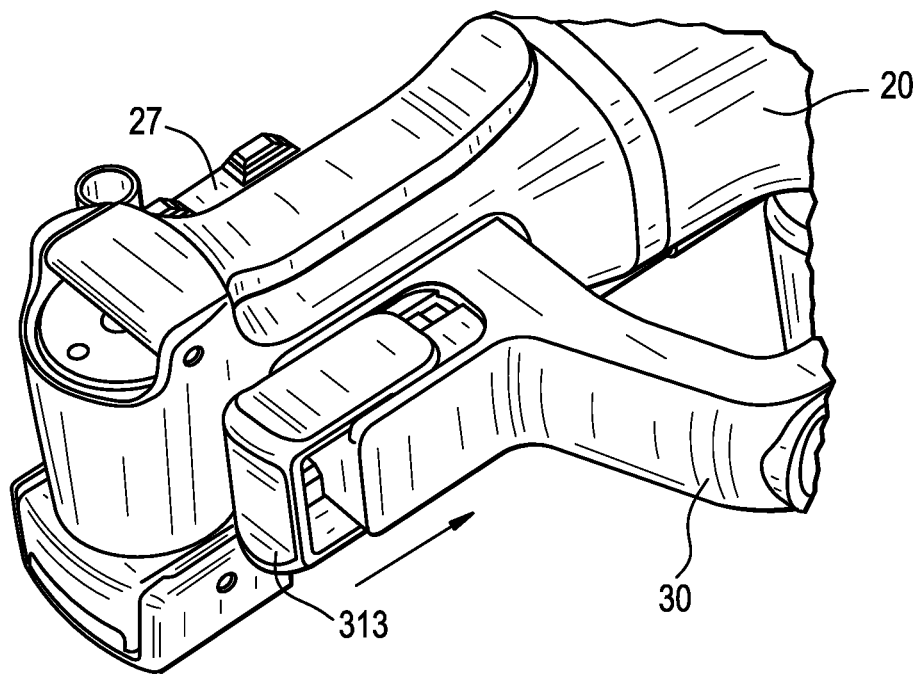

FIGS. 11A-11C illustrate steps of a method for connecting the tracker to the body using the connectors of FIGS. 9A-9B and 10A-10B.

As shown in FIG. 11A, the proximal shaft 311 of the tracker is first introduced in the housing 211 provided at the proximal end of the body, in the direction shown by the arrow, which is substantially parallel to axis X.

Then, as shown in FIG. 11B, the tracker is pivoted about the shaft 311 in the direction indicated by the arrow, so as to bring the distal end of the tracker in front of the connector 26. In this step, the slider 313 is in the unlocking position.

At last, as shown in FIG. 11C, the slider 313 is translated to the locking position, in the direction indicated by the arrow.

The tracker 30 is thus stably secured to the body 20.

To remove the tracker from the body, the previous steps have to be carried out in reverse order.

Figure 12A:
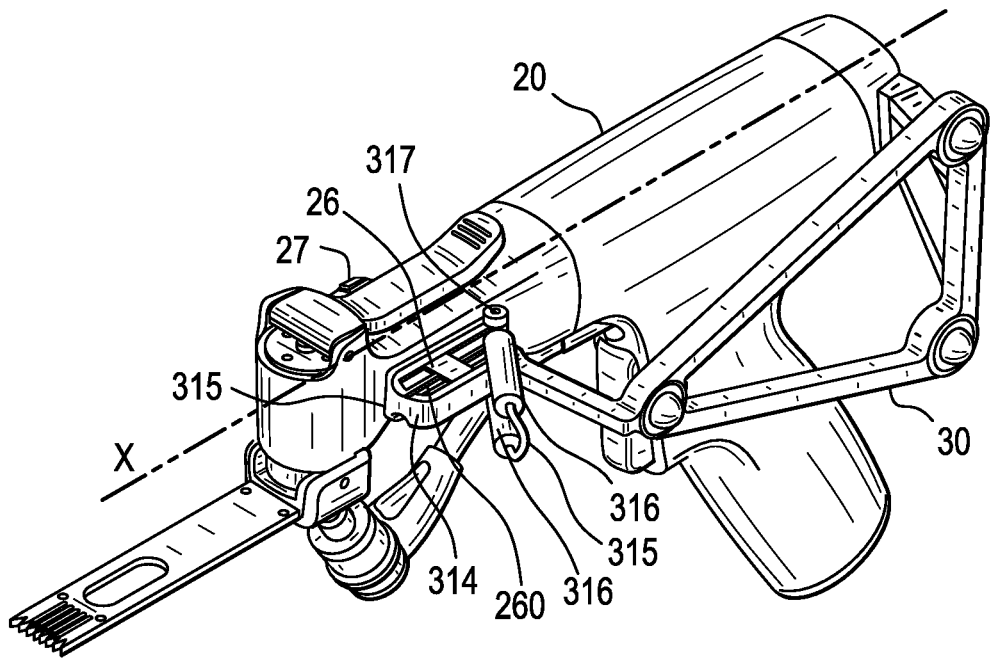
FIGS. 12A-12B illustrate an embodiment of the connection of the tracker to the distal part of the body.
Figure 12B:
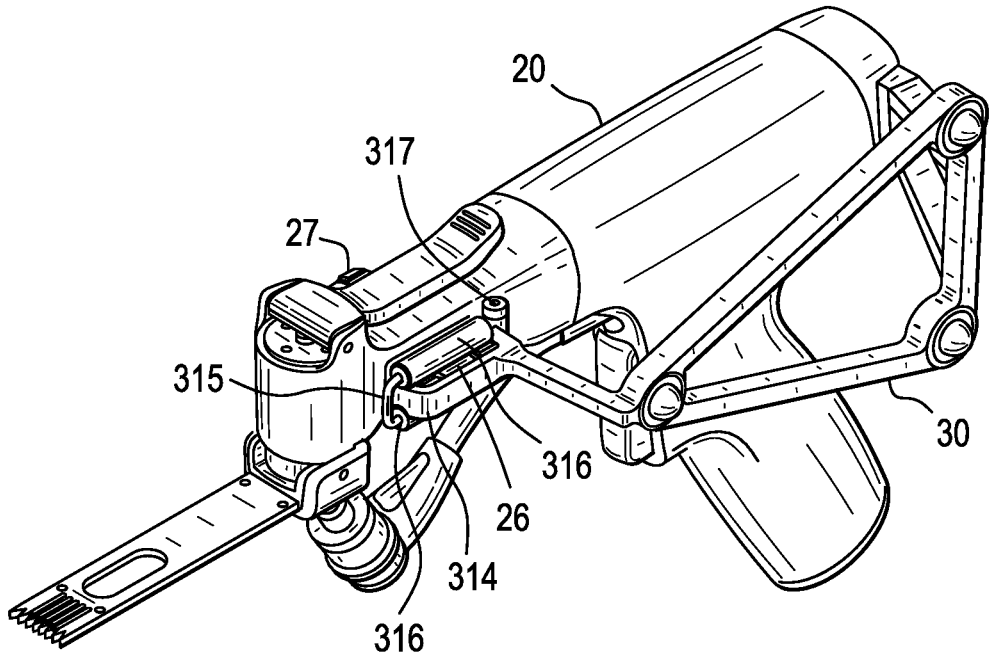

FIGS. 12A-12B illustrate another embodiment of the connection of the tracker to the distal part of the body. The connectors 26, 27 are substantially the same as the ones illustrated in FIG. 7A. In particular, the connector 26 comprises a longitudinal groove 260 on both sides (the groove 261 may be omitted in this embodiment).

The distal part of the tracker 30 comprises a plug 314 configured to engage the connector 26. The plug comprises a central opening adapted to the shape of the connector 26, so that when the tracker 30 is connected to the body 20, the plug is in contact with the body 20 and surrounds the connector 26 while leaving access to the longitudinal grooves 260.

The distal part of the tracker 30 further comprises a roller lock. The roller lock comprises a frame 315 having a rectangular shape. Rollers 316 are rotatably mounted on two opposite sides of the frame 315. The frame 315 is connected to the plug 314 by a hinge 317 which is substantially perpendicular to the longitudinal axis X of the body when the plug 214 engages the connector 26. The roller lock is thus pivotable between an unlocking position (see FIG. 12A) and a locking position (see FIG. 12B). In the locking position, the rollers 316 engage the longitudinal grooves 260 of the connector 26 and maintain the plug 314 connected to the connector 30. The transition between the unlocking position and the locking position is allowed by an elastic deformation of the frame when a push or pull force greater than a threshold is applied to the roller lock to engage or disengage the connector. For example, the frame may be formed of a metal wire which is capable of deforming in the direction of said force when said force is applied, so as to engage or disengage the rollers 316 one after the other, and to return to a rest position where the rollers are sufficiently close to each other to be retained in the grooves 260.

Figure 13:
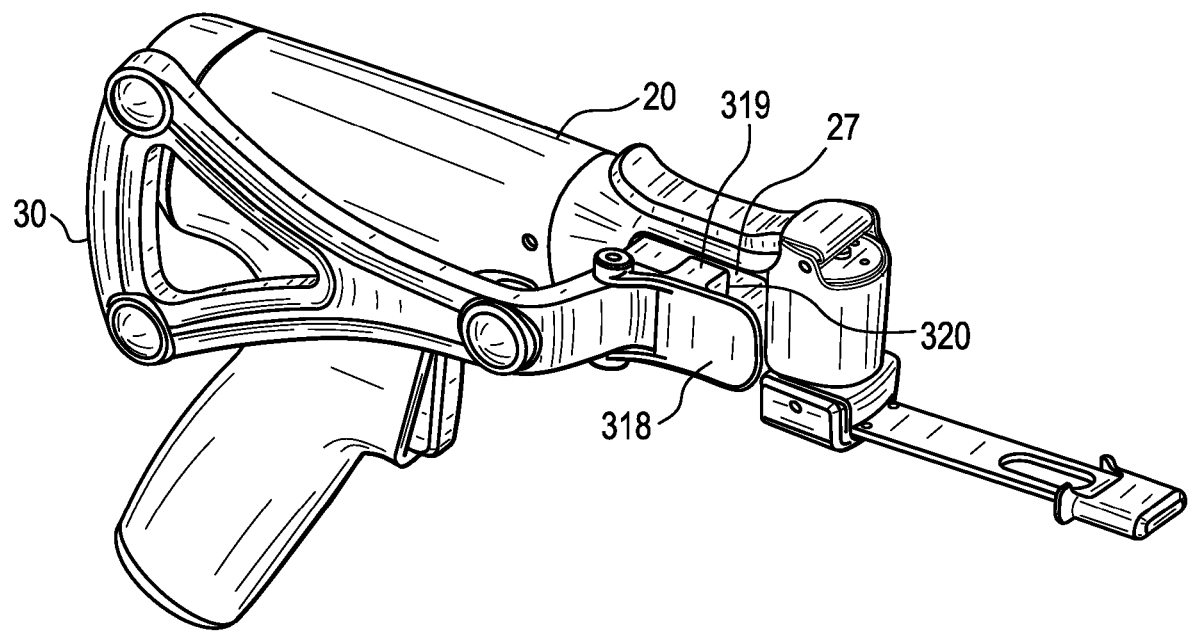
FIG. 13 illustrates an embodiment of the connection of the tracker to the distal part of the body.

FIG. 13 illustrates another embodiment of the connection of the tracker to the distal part of the body, in locking position. The distal part of the tracker 30 comprises a pivotable lock 318. Although not visible, the connectors 26, 27 are substantially the same as the ones illustrated in FIG. 7A. In particular, the connectors comprise a longitudinal groove 260 on both of their sides (the groove 261 may be omitted in this embodiment.

The pivotable lock comprises two arms configured to engage the upper and lower sides of the connector 27 (only the upper arm 319 is visible in FIG. 13). Each arm comprises a protrusion 320 extending inwardly to engage a respective longitudinal groove of the connector. The pivotable lock is advantageously made of a plastic material. The transition between the unlocking position and the locking position is allowed by an elastic deformation of the arms of the pivotable lock when a push or pull force greater than a threshold is applied to the lock to engage or disengage the connector.

Figure 14A:
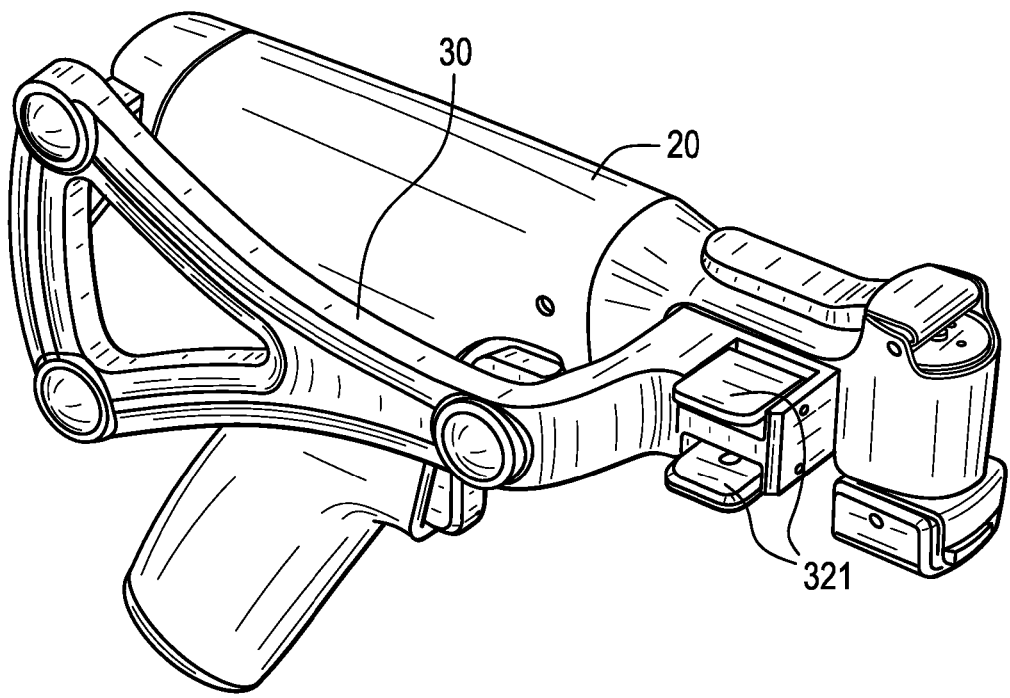
FIGS. 14A-14C illustrate an embodiment of the connection of the tracker to the distal part of the body.
Figure 14B:
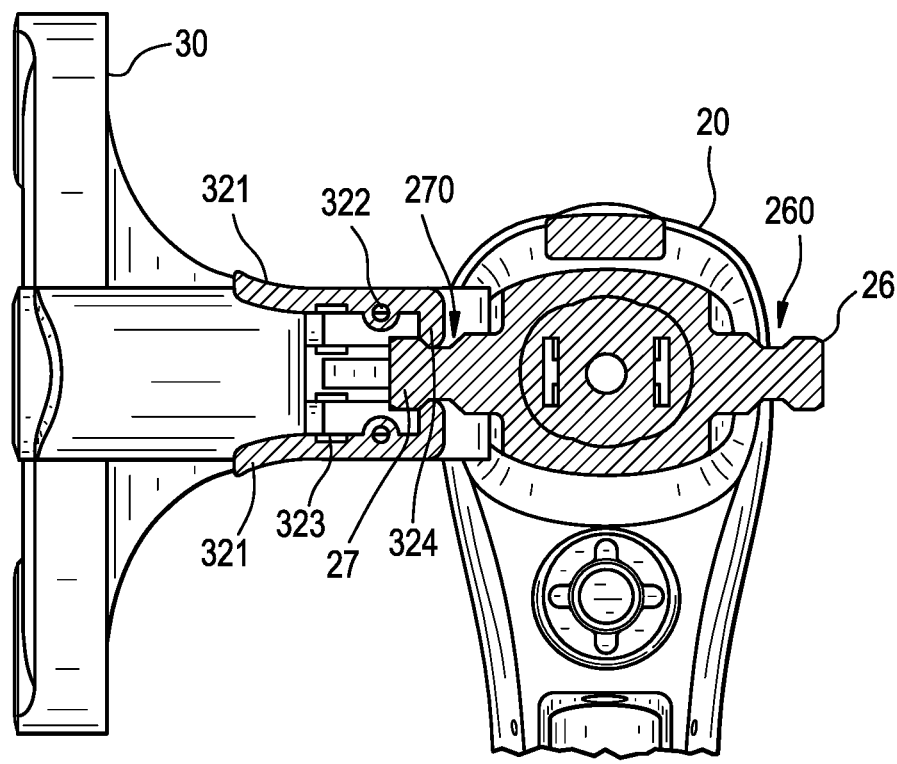
Figure 14C:
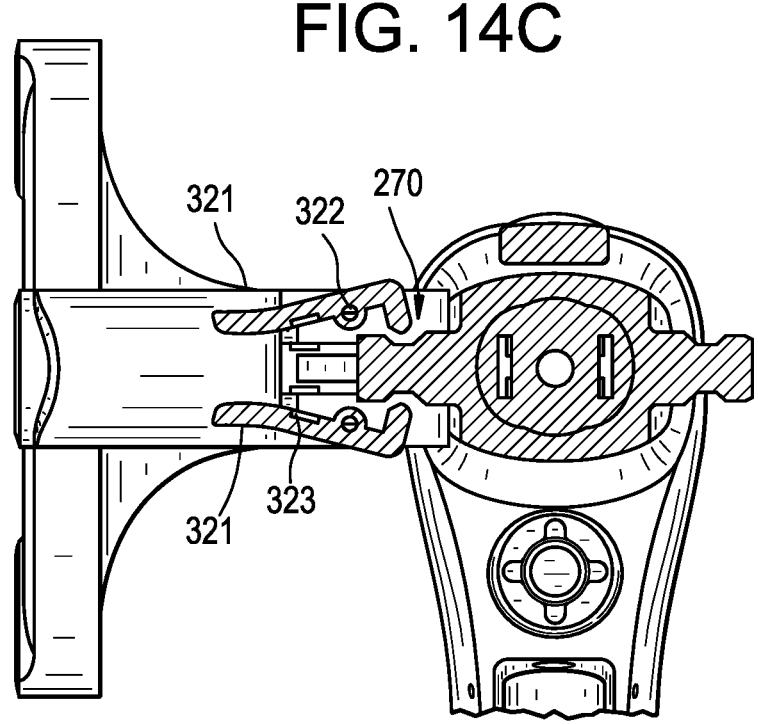

FIGS. 14-14C illustrate another embodiment of the connection of the tracker to the distal part of the body.

The distal part of the tracker comprises two wings 321 configured to engage both sides of the connector 26 or 27. Each wing 321 is pivotable about a shaft 322 which extends substantially parallel to the longitudinal axis of the body when the tracker is connected to the body. Each wing 321 comprises a finger 324 configured to engage a longitudinal groove 260 or 270 of the connector. The wings are urged in a locking position (see FIG. 14B) by a spring (not shown) arranged between the wings in housing 323. To connect or disconnect the tracker, a user has to pinch the wings 321 to space the fingers 324 apart from each other (see FIG. 14C).

In the embodiments of FIGS. 12A-14C, the tracker is first connected to the proximal end of the body, by any suitable means such as the ones described above.

FIGS. 15A-15E illustrate steps of a method for connecting the surgical tool to the robotic system.

Figure 15A:
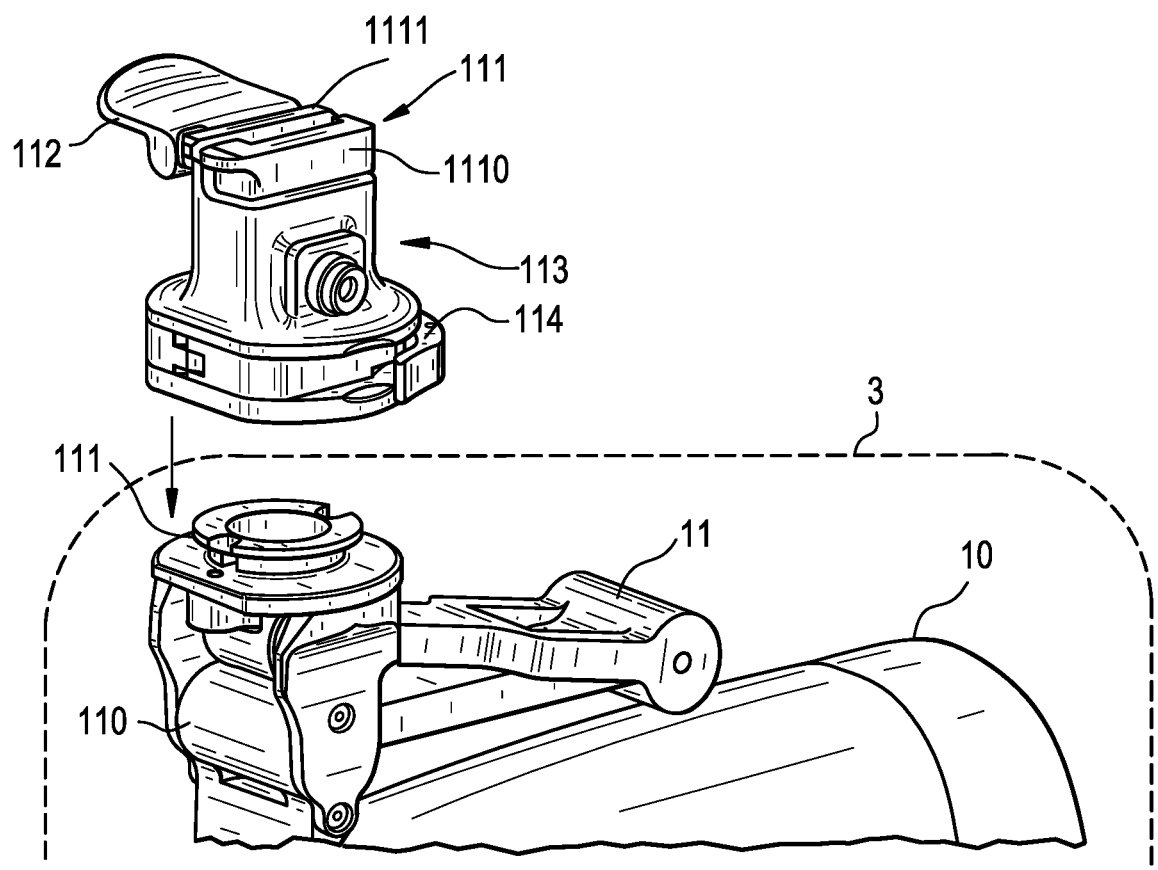
FIGS. 15A-15E illustrate steps of a method for connecting the surgical tool to the robotic system.
Figure 15B:
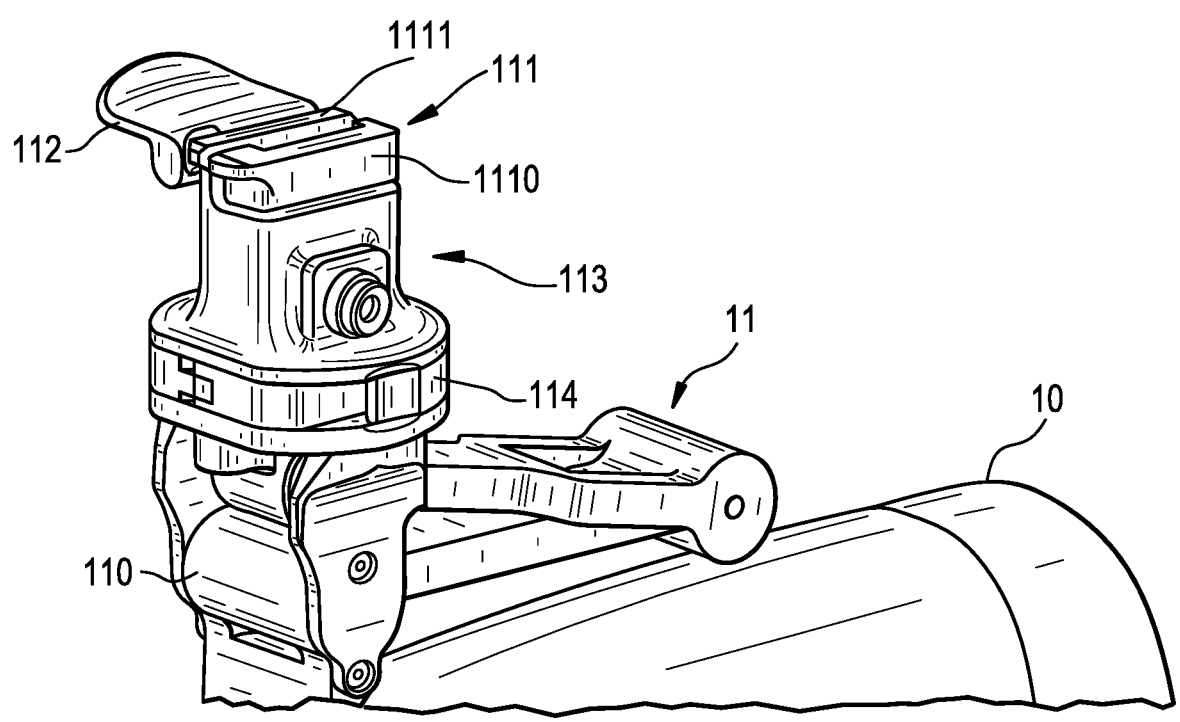

With reference to FIGS. 15A and 15B, the actuation unit 10 and planar mechanism 11 are covered by a sterile drape 3 which is schematically represented by the dotted line. Although not represented in the next figures, the sterile drape remains in place until the end of the surgical intervention.

A connecting piece 113 is connected to the end 111 of the planar mechanism, the sterile drape is clamped between the end 111 of the planar mechanism and the connecting piece 113, which is sterile. The connecting piece comprises the clamping jaws 1110, 1111 and the eccentric lever 112 of FIG. 8.

The connecting piece is secured to the planar mechanism by locking a lever 114.

Figure 15C:
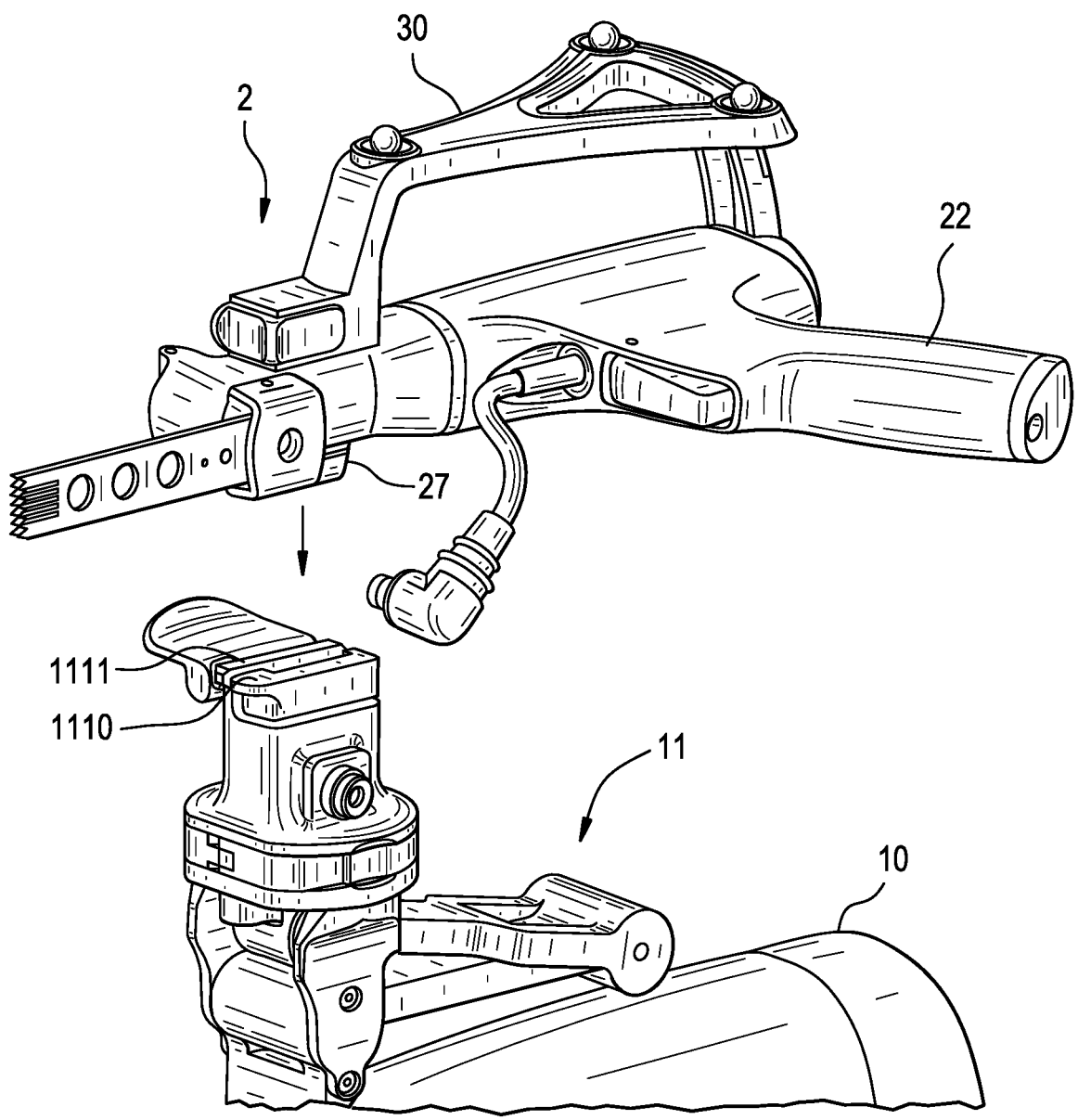

With reference to FIG. 15C, the saw 2, which has been previously equipped with the tracker 30 (e.g. as shown in FIGS. 11A-11C) is mounted to the connecting piece 113 by inserting the connector 27 into the open clamping jaws 1110, 1111.

Figure 15D:
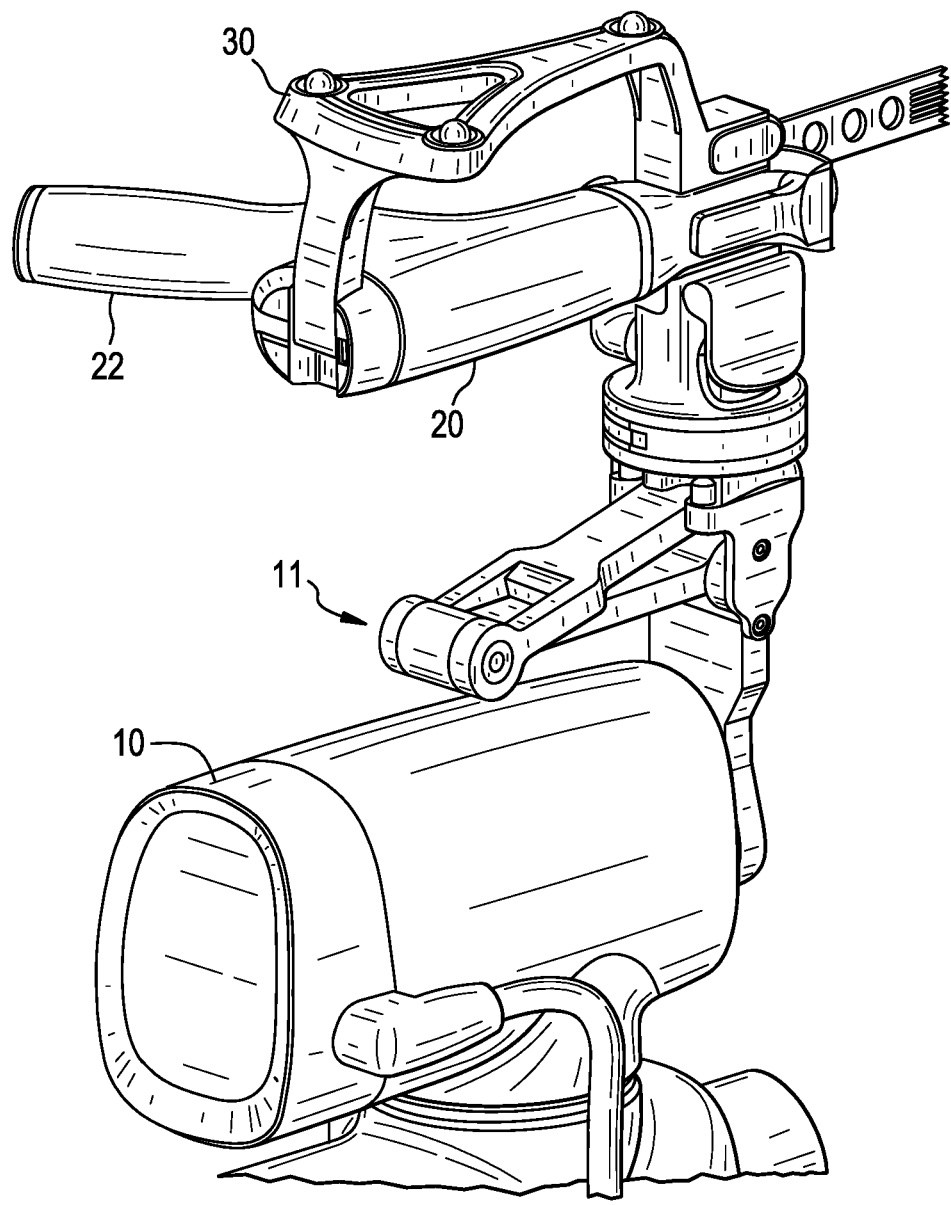

Then, as shown in FIG. 15D, the saw is secured to the connecting piece 113 by actuating the eccentric lever 112 to close the clamping jaws.

Figure 15E:
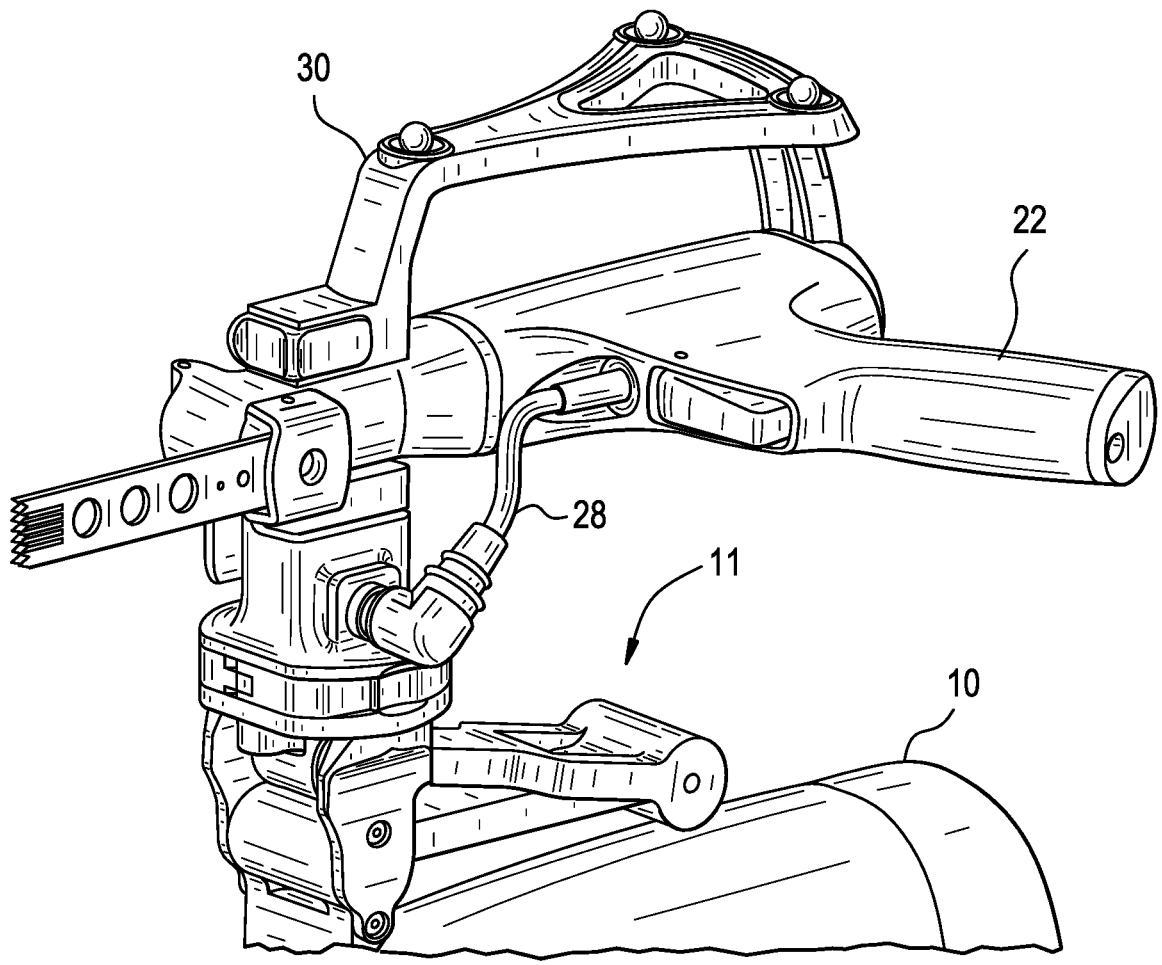

As shown in FIG. 15E, the electric cable extending from the body is electrically connected to the power system of the actuation unit via the connecting piece 113.

The robotic device is thus ready to use.

Robotic System

The surgical tool may advantageously be used in a robotic system as described in document WO 2018/103945.

Said robotic system 1 comprises a motorized actuation unit 10, a planar mechanism 11 with a first end 110 attached to a terminal segment of the actuation unit, a second end 111 rigidly attached to the surgical tool 2. The robotic system also comprises trackers 30, 31 attached to the cutting tool and to the patient to determine in real time a relative position of the end effector and the bone to be cut, and a control unit configured to compensate small movements from the patient or the surgeon, in order to achieve a planned cut.

The actuation unit 10 has a serial architecture made of a plurality of mobile segments. In some embodiments, the actuation unit has three motorized rotational degrees of freedom for adjusting the position and orientation of the cutting plane relative to each target plane. In other embodiments, the actuation unit has two motorized rotational degrees of freedom and one or two motorized translational degrees of freedom. Generally speaking, the actuation unit comprises from three to five motorized degrees of freedom, at least two of which being rotational degrees of freedom orthogonal to each other. The segments and their components are integrated in an optimal way such that the robotic device remains as compact and light as possible while remaining strong enough to be able to hold the planar mechanism and the surgical tool, as well as resisting to some normal pressure applied by the user when he/she manipulates the surgical tool.

Preferably, the architecture of the actuation unit is made of three rotational degrees of freedom.

According to a preferred architecture, the segments are arranged such that the rotation axes of two adjacent segments (i.e. either the first and second axes or the second and third axes) are substantially parallel to each other, and the first axis is substantially orthogonal to the third axis. Preferably, the rotation axes of two adjacent segments are parallel to each other and the first axis is orthogonal to the third axis.

In use for knee arthroplasty (TKA, UKA, etc.), the robotic device may be placed on the medial (internal) or on the lateral (external) side of the leg of interest. The first rotation axis is intended to be substantially orthogonal to the sagittal plane of the knee, and substantially located at the level of the medial or lateral epicondyle. For any application of the robotic system, it is possible to define some anatomical landmarks that are easy to identify and to use them for aligning the actuation unit in a ball park.

In some embodiments, the architecture of the actuation unit may enable additional movements which can be motorized or not—within the cutting plane. By excluding six motorized degrees of freedom, the invention distinguishes over large surgical robots by a lower inertia—especially according to the first axis—and thus a greater responsiveness required in particular to compensate for bone motion in real time.

As it will be explained in more details below, the actuation unit is controlled by the control unit. The control unit may be integrated in the robotic device, or remote from the robotic device.

The surgical tool is coupled to the actuation unit by a planar mechanism 11, the planar mechanism being configured to constrain the movement of the cutting tool within the cutting plane.

Advantageously, the cutting tool can be decoupled from the planar mechanism. Preferably, especially in the case where the cutting tool is not intended to receive a tracker, the attachment means for the cutting tool provides reproducible fixation.

Several different architectures exist to implement a planar mechanism. For example, the planar mechanism can be made of only one rotation axis and then one translation axis that carries the cutting tool along its longitudinal direction. Alternatively, the planar mechanism can be made of two orthogonal translation axes and then a rotational axis. According to another embodiment, the planar mechanism can be a slider in the form of an arch, including a rotation axis, and then a translation axis that carries the cutting tool.

According to an embodiment, the planar mechanism is passive, meaning that the mechanism is not motorized and can be freely manipulated by the user. One advantage of such a passive mechanism is to preserve all the perceptions of the user when the saw is manipulated in the bone. For example, surgeons are used to freely manipulate a saw in a cutting block and to detect when the saw blade has reached the back of the bone by sensing changes in the bone resistance, and this perception is fully preserved with a passive planar mechanism that has very low friction at its joints.

Alternatively, the planar mechanism may also be at least partially active, i.e. comprising at least one motorized degree of freedom. If the planar mechanism is active, i.e. it comprises at least two motorized degrees of freedom, the cut(s) can be performed automatically. It is to be noted that said motorized degrees of freedom are all configured to move the cutting tool within the cutting plane.

Whatever the embodiment, the planar mechanism may comprise a locking system for locking each of its degrees of freedom once the cutting plane has been aligned with the target plane.

The system comprises an articulated lockable holding arm 12 supporting the actuation unit and suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm is made of several articulated segments using ball-and-socket joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the cutting tool and reaction forces caused by movements of the actuation unit.

According to an embodiment, the holding arm is passive.

Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm—possibly with a braking force as described above. If a new target position of the robotic device is defined, new braking volumes are defined, and the braking is adjusted based on said new volumes.

Preferably, the connection between the holding arm and the actuation unit is as close as possible to the first segment of the actuation unit or to the center of gravity of the robotic device in order to minimize any lever-arm effect. The part of the actuation unit that is attached to the holding arm is called the base of the robotic device.

According to an embodiment, the first segment of the actuation unit may be fixed relative to the holding arm. In such case, the second segment of the actuation unit is necessarily mobile relative to the first segment. This architecture is advantageous in that it minimizes the weight of the moving components of the actuation unit. As a result, the robotic device may be more responsive, which is favorable to real time control of the cutting plane.

According to an embodiment, the first segment of the actuation unit may be mobile relative to the holding arm. In such case, the first and second segments are preferably embedded in a single housing.

The system also comprises a tracking unit configured to determine in real time the pose of the saw with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of each segment of the actuation unit is known in real time thanks to encoders or sensors of the motors, and a calibrated model of the robot that includes all axes and distances of the robot segments. Using this model, and well-known geometric modeling techniques in robotics, it is possible to calculate the relative positions of all segments, so if one measurement is known in a coordinate system attached to the robot basis using an external tracker, then any segment position is also known in the same coordinate system. Additionally, if a tracker is attached to the base of the actuation unit and a second tracker is attached to the anatomical structure, then the pose of any segment of the actuation unit is known in the coordinate system attached to the tracker of the anatomical structure.

The invention claimed is:
1. A surgical tool comprising:
a body defining a longitudinal axis;
an end-effector extending from a distal end of the body, the end-effector being movable relative to the body about a pivot axis;
a first connector configured to rigidly secure the body to a planar mechanism;
a second connector configured to rigidly secure a distal part of a tracker to the body; and
a third connector configured to rigidly secure a proximal part of the tracker to the body;
wherein the first and second connectors are symmetrical to each other with respect to a plane comprising the longitudinal axis and the pivot axis and are adapted for attachment of either the tracker or the planar mechanism.

2. The surgical tool of claim 1, wherein the body comprises a recess shaped to receive a user's palm.

3. The surgical tool of claim 1, further comprising a handle selectively pivotable relative to the body, the handle comprising a grip and a trigger configured to activate the end-effector.

4. The surgical tool of claim 3, wherein the handle is selectively pivotable about an axis orthogonal to the longitudinal axis.

5. The surgical tool of claim 3, wherein the handle comprises two triggers configured to activate the end-effector, a first trigger being located on a distal side of the handle and a second trigger being located on a proximal side of the handle, the first trigger being closer to the body than the second trigger.

6. The surgical tool of claim 3, wherein the handle is selectively pivotable about the longitudinal axis.

7. The surgical tool of claim 6, wherein the handle has a substantially U shape, the handle comprising:
a distal arm pivotally coupled to the body about the longitudinal axis;
a proximal arm comprising the grip and the trigger; and
a bridge connecting the distal arm and the proximal arm such that the proximal arm is offset from a proximal end of the body.

8. A robotic system comprising:
a lockable holding arm;
an actuation unit coupled to the holding arm;
a planar mechanism coupled to the actuation unit;
the surgical tool of claim 1, wherein the body is rigidly secured to the planar mechanism by the first connector; and
a tracker rigidly attached to the body of the surgical tool by the second and third connectors.

9. The robotic system of claim 8, wherein the tracker extends substantially parallel to a side of the body, the tracker and the second connector being configured so as to define a gap sufficient to pass a user's fingers between the body and the tracker.

10. The robotic system of claim 8, wherein the distal part of the tracker comprises a plug configured to engage the first or second connector and a roller lock including a frame and two rollers rotatably mounted on opposite sides of the frame, the frame being pivotable relative to the plug between a locking position wherein the rollers engage longitudinal grooves of the first or second connector and an unlocking position, the frame being deformable to allow engaging or disengaging the rollers one after the other in a respective longitudinal groove.

11. The robotic system of claim 8, wherein the proximal end of the tracker comprises upper and lower arms connected by a tongue and upper and lower levers extending from each respective arm, and the third connector comprises opposite upper and lower recesses and opposite right and left grooves, the arms being positioned around the third connector and the tongue engaging one of the right and left grooves, the levers being movable between an unlocking position not interfering with the third connector and a locking position where each lever engages a respective recess of the third connector.

12. The robotic system of claim 8, wherein the proximal end of the tracker comprises left and right arms fitting the third connector, each arm comprising a flange extending in a distal direction and including an inner rim, and the body comprises right and left grooves engaging a respective rim.

13. The robotic system of claim 8, wherein the proximal end of the tracker comprises a shaft configured to be pivotally mounted into a housing of the third connector, the shaft having a non-circular cross section and the housing comprising a slot configured for inserting the shaft in a first orientation and retaining the shaft in a second orientation angularly offset from the first orientation.

14. The robotic system of claim 8, wherein the planar mechanism comprises a connector configured to engage either the first or the second connector, comprising clamping jaws mobile relative to each other between open and closed positions and having an internal shape complementary to an outer shape of the first and second connectors, the connector further comprising a pivotable eccentric lever configured to cause the jaws to close against a spring force.

15. The robotic system of claim 8, wherein the tracker is an optical tracker.

16. The robotic system of claim 8, wherein the tracker is a single use tracker made of a plastic material.

17. A robotic system comprising:
- a surgical tool comprising:
  - a body defining a longitudinal axis;
  - a handle selectively pivotable relative to the body;
  - an end-effector extending from a distal end of the body;
  - a pair of symmetrical first and second connectors disposed on either side of the body adjacent to the distal end; and
  - a third connector disposed on a proximal end of the body; and
- a tracker that attaches pivotably to the third connector at a proximal part of the tracker, a distal part of the tracker adapted for tool-less attachment to the first connector or the second connector, such that the tracker is attached to the body using two connectors.

18. The robotic system of claim 17, wherein the distal part of the tracker has a pair of deformable members to release the tracker from the first connector or the second connector.

19. The robotic system of claim 17, wherein the distal part of the tracker has a slider to release the tracker from the first connector or the second connector.

20. The robotic system of claim 17, wherein the proximal part of the tracker has a shaft that does not have a circular cross section, such that the shaft is retained in the third connector when the tracker pivots to engage the first connector or the second connector.

* * * * *